US011568995B1

(12) United States Patent
Lavi et al.

(10) Patent No.: US 11,568,995 B1
(45) Date of Patent: *Jan. 31, 2023

(54) INDIRECT BIO-FEEDBACK HEALTH AND FITNESS MANAGEMENT SYSTEM

(71) Applicants: Natan Lavi, Cupertino, CA (US); Dan Ariely, Durham, NC (US)

(72) Inventors: Natan Lavi, Cupertino, CA (US); Dan Ariely, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/573,422

(22) Filed: Jan. 11, 2022

Related U.S. Application Data

(63) Continuation of application No. 17/142,188, filed on Jan. 5, 2021, now Pat. No. 11,222,730, which is a (Continued)

(51) Int. Cl.
*G16H 50/30* (2018.01)
*G16H 40/67* (2018.01)
(Continued)

(52) U.S. Cl.
CPC ......... *G16H 50/30* (2018.01); *A61B 5/14532* (2013.01); *A61B 5/743* (2013.01); *G16H 40/67* (2018.01)

(58) Field of Classification Search
CPC ........ G16H 50/30; G16H 40/67; G16H 20/60; A61B 5/14532; A61B 5/0537;
(Continued)

(56) References Cited

U.S. PATENT DOCUMENTS 5,435,315 A    7/1995    McPhee
7,557,311 B2    7/2009    Umemoto
(Continued)

FOREIGN PATENT DOCUMENTS

WO    WO2011103344    8/2011

OTHER PUBLICATIONS

"Bollinger Bands". Wikipedia.org. [dated Nov. 9, 2014], [online], [retrieved on Jun. 11, 2018]. <URL:https://web.archive.org/web/20141109125702/https://en.wikipedia.org/wiki/Bollinger_Bands>. 6 Pages.

*Primary Examiner* — Milap Shah
(74) *Attorney, Agent, or Firm* — Allen D. Hertz, P.A.; Allen D. Hertz

(57) ABSTRACT

A health and fitness management system that employs an algorithm to determine suggested recommended actions for a user to improve their health and fitness. The system obtains a user's health indicating measurement from a respective acquisition device. The user is never informed of the acquired data. The health indicating measurement can include a heart/pulse rate, blood pressure measurement, weight, etc. Base line data (age, ideal age, initial weight, current weight, ideal weight, etc.) can be considered in the algorithm. Examples include the user's environment, sleep habits, exercise routines, medical records, and the like. The health index number is used to determine recommended actions, which can include changes to environments, routines, activities, etc. Data collection, the algorithm, and other features of the system can be provided by an Application operating on a portable computing device. Features of the portable computing device can be employed to automatically acquire data for the algorithm.

1 Claim, 19 Drawing Sheets

Related U.S. Application Data continuation-in-part of application No. 16/506,740, filed on Jul. 9, 2019, now Pat. No. 10,885,807, which is a continuation-in-part of application No. 15/364,220, filed on Nov. 29, 2016, now Pat. No. 10,347,152.

(60) Provisional application No. 62/262,354, filed on Dec. 2, 2015.

(51) Int. Cl.
*A61B 5/00* (2006.01)
*A61B 5/145* (2006.01)

(58) Field of Classification Search
CPC ......... A61B 5/4872; A61B 5/74; A61B 5/742; A61B 5/743; G06F 17/11; G01G 19/4146; G01G 19/44; G01G 23/3728; G09B 19/0092; G09B 19/3418; G09B 19/3475; G09B 19/3481
See application file for complete search history.

(56) References Cited

U.S. PATENT DOCUMENTS

| | | | |
|---|---|---|---|
| 8,200,453 B2 | 6/2012 | Gage | |
| 8,475,367 B1 | 7/2013 | Yuen | |
| 8,538,772 B2 | 9/2013 | Sato | |
| 8,560,479 B2 | 10/2013 | Bosworth | |
| 9,232,915 B2 | 1/2016 | Chua | |
| 9,370,689 B2 | 6/2016 | Guillama | |
| 9,433,357 B2 | 9/2016 | Yuen | |
| 9,546,898 B2 | 1/2017 | Kovacs | |
| 9,656,144 B2 | 5/2017 | Jafarifesharaki | |
| 9,693,696 B2 | 7/2017 | Kovacs | |
| 9,891,095 B2 | 2/2018 | Villard | |
| 9,984,588 B1 | 5/2018 | Barker | |
| 10,215,619 B1 | 2/2019 | Kovacs | |
| 10,347,152 B2 | 7/2019 | Lavi | |
| 10,885,807 B1 | 1/2021 | Lavi | |
| 11,222,730 B1* | 1/2022 | Lavi | A61B 5/743 |
| 2004/0238641 A1 | 12/2004 | Harima | |
| 2005/0060194 A1 | 3/2005 | Brown | |
| 2005/0247494 A1 | 11/2005 | Montagnino | |
| 2006/0206013 A1 | 9/2006 | Rothman | |
| 2008/0091463 A1 | 4/2008 | Shakamuri | |
| 2008/0154645 A1 | 6/2008 | Takehara | |
| 2008/0162352 A1* | 7/2008 | Gizewski | G16Z 99/00 705/50 |
| 2008/0171584 A1 | 7/2008 | Roberts | |
| 2008/0208015 A1 | 8/2008 | Morris | |
| 2009/0105550 A1 | 4/2009 | Rothman | |
| 2010/0049471 A1 | 2/2010 | Gage | |
| 2010/0184565 A1 | 7/2010 | Avellino | |
| 2010/0317488 A1 | 12/2010 | Cartaya | |
| 2011/0201901 A1 | 8/2011 | Khanuja | |
| 2011/0263993 A1 | 10/2011 | Martikka | |
| 2012/0078652 A1 | 3/2012 | Konishi | |
| 2012/0123797 A1 | 5/2012 | Sock | |
| 2012/0130198 A1 | 5/2012 | Beaule | |
| 2012/0296455 A1 | 11/2012 | Ohnemus | |
| 2013/0101966 A1 | 4/2013 | Sreenivasan | |
| 2013/0211858 A1 | 8/2013 | Ohnemus | |
| 2013/0311197 A1 | 11/2013 | Hummer | |
| 2014/0074510 A1 | 3/2014 | McClung | |
| 2014/0088444 A1 | 3/2014 | Saalasti | |
| 2014/0135592 A1 | 5/2014 | Ohnemus | |
| 2014/0324443 A1 | 10/2014 | Ricks | |
| 2014/0344192 A1 | 11/2014 | Akai | |
| 2015/0093725 A1 | 4/2015 | Baarman | |
| 2015/0339949 A1 | 11/2015 | Landers | |
| 2015/0370986 A1 | 12/2015 | Hayward | |
| 2015/0374267 A1 | 12/2015 | Laughlin | |
| 2016/0055758 A1 | 2/2016 | Francis | |
| 2016/0317074 A1 | 11/2016 | Kawai | |
| 2016/0371453 A1 | 12/2016 | Bowman | |
| 2017/0098040 A1 | 4/2017 | Wolin | |
| 2017/0147775 A1 | 5/2017 | Ohnemus | |
| 2018/0233223 A1 | 8/2018 | Solari | |
| 2021/0128061 A1 | 5/2021 | Joseph | |
| 2022/0230741 A1* | 7/2022 | Wynnik | G16H 40/67 |

* cited by examiner

INDIRECT BIO-FEEDBACK HEALTH AND FITNESS MANAGEMENT SYSTEM

CROSS REFERENCE TO RELATED APPLICATION

This Non-Provisional Patent Application claims a common domestic benefit as follows:

wherein this Non-Provisional Utility Patent Application is a Continuing Prosecution Application claiming the benefit of co-pending U.S. Non-Provisional Patent Application Ser. No. 17/142,188, filed on Jan. 05, 2021 (scheduled to issue as U.S. Patent 11,222,730 on Jan. 11, 2022), wherein U.S. Non-Provisional Patent Application Ser. No. 17/142,188 is a Continuation-In-Part claiming the benefit of U.S. Non-Provisional Patent Application Ser. No. 16/506,740, filed on Jul. 09, 2019 (now U.S. Patent 10,885,807, issued on Jan. 05, 2021), wherein U.S. Non-Provisional Patent Application Ser. No. 16/506,740 is a Continuation-In-Part claiming the benefit of U.S. Non-Provisional Patent Application Ser. No. 15/364,220, filed on Nov. 29, 2016 (now U.S. Patent 10,364,220, issued on Jul. 09, 2019), wherein U.S. Non-Provisional Patent Application Ser. No. 15/364,220 claims the benefit of U.S. Provisional Patent Application Ser. No. 62/262,354, filed on Dec. 02, 2015, wherein the entireties each of above the above applications are incorporated herein by reference.

FIELD OF THE INVENTION

The present disclosure generally relates to a system that collects data associated with an individual's health and well being, utilizes the collected data to provide guidance to the individual, all while isolating the actual data from the individual to avoid any potential psychological implications from knowledge of the actual data.

BACKGROUND OF THE INVENTION

Health and fitness are one significant focus of a majority of people. Health and fitness are attributed to diet, exercise, and daily routines. A major hurdle in the creation of a lifestyle that is conducive to improved health and fitness is a daunting psychological effect of exposure to data, such as weight, caloric intake, calories burned, and the like.

The U.S. Department of Health and Human Services has found that nearly 7 in 10 adults in the U.S. are overweight or obese (69%, 2011-2012). The market for weight-loss which includes diet books, diet drugs and weight-loss surgeries is estimated at $20B. Furthermore, the medical cost associated with obesity was $147B (CDC, 2008).

There has been an enormous amount of research into diet, genetics, behavior that has yielded valuable insights, strategies, and techniques for losing weight. And, there are countless approaches for tackling weight loss based on this research. However, none of these approaches has overcome the challenge of sustained weight loss and improved health.

Motivation for any long-term behavioral change requires the feeling of success and progress. In the domain of weight loss there is a large gap between what people do, and how successful they feel. People can give up sweets, but any weight loss would not show up for a while, and when it does, it will be a slow progress. People can start exercising, but initially they might even gain weight. More generally, biological systems, such as out body, react slowly and in a stochastic way to any behavioral changes.

What is desired is a system that changes the type and frequency of feedback to give people more useful information and make them celebrate more clearly when they are successful.

What is desired is a system to provide guidance to an individual to modify their diet, exercise routine, and daily activities to improve their overall health and fitness.

DESCRIPTION OF THE INVENTION

The general concept behind the present invention is to provide a system for collecting data and lifecycle patterns to provide guidance to an individual to modify their diet, exercise routine, and daily activities to improve their overall health and fitness. The collected data would be analyzed to provide feedback to the individual without exposing the individual to the actual collected data. This avoids any psychological implications.

The health and fitness management system is an intelligent behavioral platform that learns about a user's health, behaviors, and other aspect of their life, suggests ways to improve their health, and provides feedback in a way that is more effective for making lasting behavioral changes.

This approach encourages behavior that is conducive to better fitness and health, and to modify the individual's habits to healthier habits over time, while avoiding any possibility of negative feeling that may serve as an excuse to return to the individual's unhealthy habits. The system avoids plateaus or steps back; only presenting actionable suggestions and feedback designed to modify the individual's behavior to a more favorable one that aims directly at the right targets that were specified by the system.

In one aspect of the present invention, the system collects the following information:

Individual's Current Age [Age(C)]
Individual's Ideal Age [Age(I)]
Individual's Starting or Initial Weight [Weight(S)]
Individual's Current Weight [Weight(C)]
Individual's Ideal Weight [Weight(I)]
Numerical multiplier [Factor]

In a second aspect of the present invention, the system utilizes the collected information to determine an effective loss in age, wherein the effective loss in age is calculated using an effective loss in age equation of:

$$\text{Effective Loss In Age} = \frac{[\text{Weight}(S) - \text{Weight}(C)]}{[\text{Weight}(S) - \text{Weight}(I)]} * [(\text{Age}(C) * \text{factor}) - \text{Age}(I)]$$

In another aspect, the system utilizes the collected information to determine a health index number, wherein the health index number is calculated using a health index number equation of:

$$\text{Health Index Number} = \text{Age}(C) - \frac{[\text{Weight}(S) - \text{Weight}(C)]}{[\text{Weight}(S) - \text{Weight}(I)]} * [(\text{Age}(C) * \text{factor}) - \text{Age}(I)]$$

In yet another aspect of the present invention, the system utilizes the collected information to determine an effective loss in age, wherein the effective loss in age is calculated using an effective loss in age equation of:

Effective Loss In Age =

$$\frac{[\text{Weight}(S) - \text{Weight}(C)]}{[\text{Weight}(S) - \text{Weight}(I)]} * [(\text{Age}(C) - \text{Age}(I)) * \text{factor}]$$

In yet another aspect, the system utilizes the collected information to determine a health index number, wherein the health index number is calculated using a health index number equation of:

Health Index Number =

$$\text{Age}(C) - \frac{[\text{Weight}(S) - \text{Weight}(C)]}{[\text{Weight}(S) - \text{Weight}(I)]} * [(\text{Age}(C) - \text{Age}(I)) * \text{factor}]$$

In yet another aspect, the system utilizes Bollinger bands.

In yet another aspect, the system employs a scale exclusive of a numeric display, wherein the scale is designed to avoid presentation of the individual's weight to the individual. The scale would be a digital scale, acquiring a weight of an individual, and converting the weight into a digital format.

In yet another aspect, the system employs activity trackers, pedometers, and the like. The data acquisition device would be adapted to retain the information and avoid presentation of the collected data to the Individual.

In yet another aspect, the system employs global positioning systems (GPS) to collect a geographic history of locations visiting by the individual, time spent at each associated geographic location, and the like.

In yet another aspect, the system cross references global positioning systems (GPS) to determine an association with the GPS location, such as restaurants, gyms, stores, and the like.

In yet another aspect, the system employs location beacons to collect a geographic history of locations visiting by the individual, time spent at each associated geographic location, and the like. Aspect information associated with each beacon can be determined by information transmitted by each respective beacon.

In yet another aspect, the system can determine travel and activity history through social media activities.

In yet another aspect, the system can obtain measurements of physical characteristics of the individual, including weight, height, sex, race, and the like.

In yet another aspect, the system can obtain information pertaining to an individual's daily routines, including sleeping habits, when the individual bathes, when the individual brushes their teeth, work hours, and the like.

In yet another aspect, the system employs one or more vital signs of the individual, including temperature, heart rate, blood pressure, and the like.

In yet another aspect, each data acquisition device would be adapted to retain the information and avoid presentation of the collected data to the Individual.

In yet another aspect, the data acquired by each data collection device can be stored within the data acquisition device or transferred to a data collection device, such as a portable computing device (Smartphone, portable computing tablet, and the like). The data could be uploaded to a portable computing device using wired or wireless technology. The collected data would eventually be transferred to a device operating an associated software or application.

In yet another aspect, the system employs a questionnaire to acquire personal information pertaining to the individual.

In yet another aspect, the system includes a questionnaire directed towards discover a user's health goals, their likes and dislikes, their medical history, they employment status, and other relevant information.

In yet another aspect, the system employs a pattern recognition module. The pattern recognition module exercises a combination of fixed rules (e.g. fast-food ==bad habit) with machine-learning (e.g. typical weekly fluctuations predict X, but actual datum was Y) to identify meaningful information about the user's behavior and habits.

In yet another aspect, the system employs a behavioral modification recommendation module. The behavioral modification recommendation module cross references information provided by at least one of the health index number and the pattern recognition module to determine optimal feedback that is most likely to improve the individual's behavior.

In yet another aspect, the system collects information and separates data points into a number of categories, including:

1. Technical requests—these may include a request to step on the scale tomorrow (if the user forgot to do so), recharge the battery on a device, etc.

2. Health advice—this may include suggestion to avoid fast-food (sent strategically right before lunch time), go to the gym more often, walk more steps tomorrow, etc.

3. Social challenges—these allow one user or a group of users to issue challenges or tasks to other users (either as a closed group, or public) to perform a certain tasks or compete with certain benchmarks, such as: who walks more steps tomorrow, abstain from sweets for a week, etc.

4. Commercial offers—these are offers from health-conscious company (organic foods, fitness supplement, etc) and local health professional (personal trainers, yoga studios) that offer services at a discount to the user.

5. Any other suitable category.

In yet another aspect, the database of available feedback option is maintained continuously and carefully curated, both manually and automatically (algorithmically) review the database for relevance, uniqueness and positive impact.

In yet another aspect, collected data is forwarded to an intelligent decision engine. The an intelligent decision engine utilizes the individual's recent behavior patterns and past response to various feedback to select from among the curated content options and determine optimal feedback, at an optimal time, to be sent to the individual using a push notification to an Individual's Smartphone, portable computing tablet, by way of an application, an email, a text message (SMS, MMS, and the like), an audible message, or any other suitable communication method.

In yet another aspect, the intelligent decision engine maintains a proper balance between the amount of content (enough to modify behavior, but not an excessive amount that would be ignored), a variety of types of content (for example: ensuring commercial offers comprise 20% of less of all feedback notifications), and relevance of content (for example: recommending more activity to sedentary individuals, and healthier eating choices to fast-food aficionados), while making sure each feedback notification arrives at an optimal time to create the greatest impact. This can include: food choices before meal-time, exercise choices before the individual leaves work, reminders not to overeat before weekends and holidays, and the like.

In yet another aspect, the system can provide an interface for commercial entities (merchants) to introduce incentives that the intelligent decision engine can include with the directive behavior modification forwarded to individuals to further aid in causing a change in the Individual's habits. The forwarded information allows each commercial provider to specify details about their offer (for example: 20% off a gym membership), times and instances when it is likely to be more relevant (for example: after a major holiday) and the like.

In yet another aspect, the system can enable a financial return to the system service provider, wherein the merchant would pay $0.10 for each click through from the Application to the associated website, $10 for each membership actually sold as a result of the information provided by the Application, and the like.

In yet another aspect, each merchant would manage offers provided thereby, including sources of each lead, history of each lead, conclusion of each lead, and any associated referral payment(s) for each lead.

In yet another aspect, each merchant would manage results of each offer in order to optimize offers/incentives and their associated frequencies to the Individuals.

In yet another aspect, the system analyzes the data over any suitable cyclic time span, such as weekly cycles, monthly cycles, annual cycles and any other suitable cycle time span.

In yet another aspect, the health state of the user can be presented in a form of a color.

In yet another aspect, the system can utilize a user's statistical z-score. The z-score is a normalized, quantitative value for determining the health status of a user.

In yet another aspect, the system can utilize the following blood pressure based algorithm to calculate the user's statistical z-score as follows:

$$z\text{-score}=(Latest\_Blood\_Pressure-mean)/std\_dev$$

Where:
Latest_Blood_Pressure=The average of the user's last 10 measurements
   mean=The mean of the user's last 30 measurements
   std_dev=The standard deviation of the user's last 30 measurements In yet another aspect, the z-score calculation above can be mapped to a representative color in accordance with the following:

$$z\text{-score}<-1.0 \Rightarrow \text{BLUE}$$

$$-1.0<=z\text{-score}<-0.5 \Rightarrow \text{TEAL}$$

$$-0.5<=z\text{-score}<0.5 \Rightarrow \text{GREEN}$$

$$0.5<=z\text{-score}<1.0 \Rightarrow \text{GRAY}$$

$$z\text{-score}>=1.0 \Rightarrow \text{DARK GRAY}$$

In yet another aspect, the color representation can also be applied to a user's weight.

In yet another aspect, the system can use the following algorithm to calculate the user's statistical z-score:

$$z\text{-score}=(Latest\_Weight-mean)/std\_dev$$

Where:
Latest_Weight=The average of the user's last 6 measurements
   mean=The mean of the user's last 20 measurements
   std_dev=The standard deviation of the user's last 20 measurements When using a color, the z-score calculation above is then mapped to a respective color such as by the following example:

$$z\text{-score}<-1.0 \Rightarrow \text{BLUE}$$

$$-1.0<=z\text{-score}<-0.5 \Rightarrow \text{TEAL}$$

$$-0.5<=z\text{-score}<0.5 \Rightarrow \text{GREEN}$$

$$0.5<=z\text{-score}<1.0 \Rightarrow \text{GRAY}$$

$$z\text{-score}>=1.0 \Rightarrow \text{DARK GRAY}$$

One significant advantage of the proposed system is the process of decoupling raw data from actionable feedback. Traditional biofeedback systems instantaneously provide actual feedback to the individual. Initially, it is noted that providing the actual data to the individual could cause a negative initial emotional reaction, deterring the individual from proceeding. Assuming the data does not deter the individual, the individual would then make the best use of the actual data and make what is believes to be optimal decisions therefrom. This option relies upon the individual's understanding of how to determine an optimal process. Conversely, the proposed system provides actionable feedback, as opposed to providing the raw data to the individual. This separates any emotional reaction as well as any self imposed considerations of the individual from the process.

The current process relies upon the basis that the individual is capable of determining the optimal process. The concern is that the individual has been adhering to certain habits that have placed them into the current health condition they are in. Following the same course of action and expecting different results is ludicrous. Introducing an impartial observer exercising sound judgment can guide the individual to achieving superior results. This is a result of the ability to avoid psychological effects and cognitive biases. The proposed system provides guidance from a viewpoint of an impartial observer.

The current process emphasizes the indirect (and sometimes lax) linking between collected data and feedback, and at times (even when the recorded data shows a clear step backward) may not reflect the collected data in the feedback it provides. The consistent goal of the system is to urge the individual towards healthier behavior habits over time. Sometimes a hard truth may be the most efficient way to change an individual's behavior; other times, a deviation from the truth may provide better results. It is imperative to include a feedback system that is followed by the individual for long periods of time to learn from the individual's past behavior, recognize patterns, and identify the optimal modes of feedback for each specific individual; without propagating raw data blindly for the individual to process them self.

The present invention utilizes at least one biometric screening device, where the at least one biometric screening device acquires the respective data. The at least one biometric screening device excludes any means (a display, an announcer, a printer, and the like) for conveying the acquired biometric test data to the individual. Examples of biometric screening devices include a scale (for measuring an individual's weight), a heart monitor, a blood pressure monitor, a glucose meter, and the like.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

When an Individual focus' on improving their health and fitness, they commonly rely upon data collection to determine improvements thereof. Data collection could be discouraging, interpreted incorrectly, or cause any other result misdirecting the progress of improving an individual's health and fitness. The present invention overcomes the deficiencies of the current solutions by defining and utilizing a health index number to aid an application in determining recommendations for the individual to improve their health and fitness.

Figure 1:
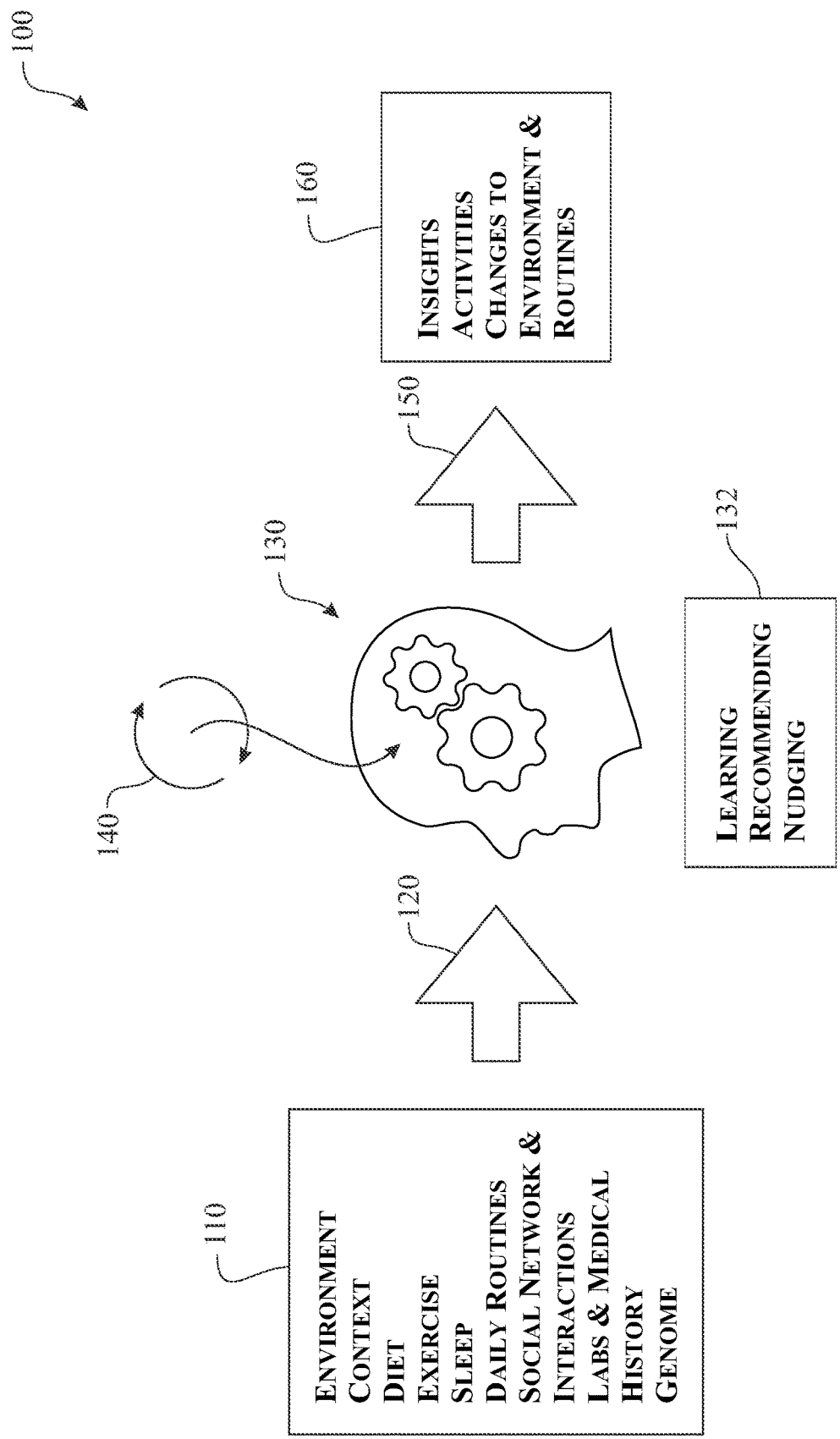
FIG. 1 presents an schematic diagram of an operational process flow of an exemplary health and fitness management system in accordance with the present invention.
Figure 2:
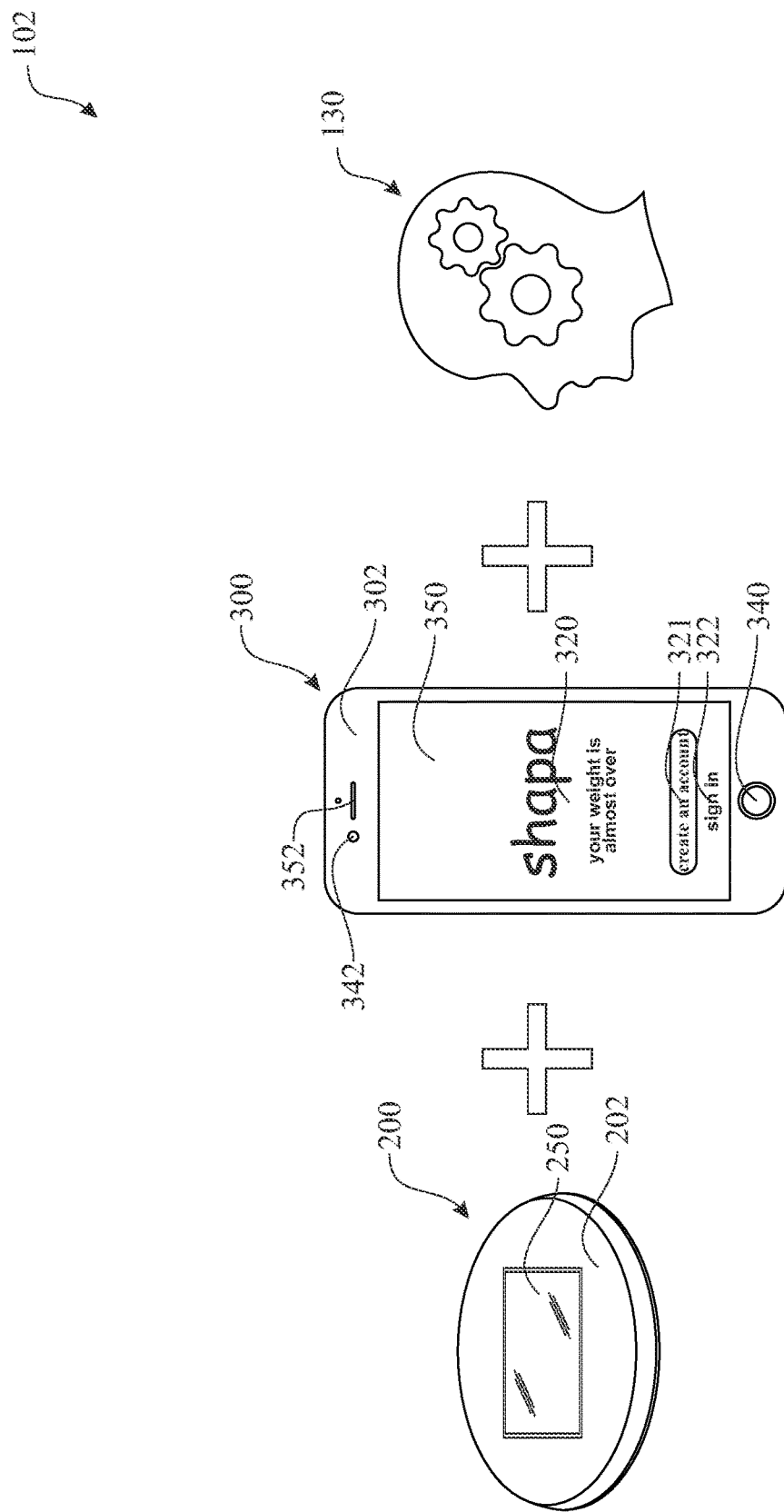
FIG. 2 presents a schematic diagram of first exemplary series of components employed by the exemplary health and fitness management system associated with the operational process flow introduced in FIG. 1.
Figure 3:
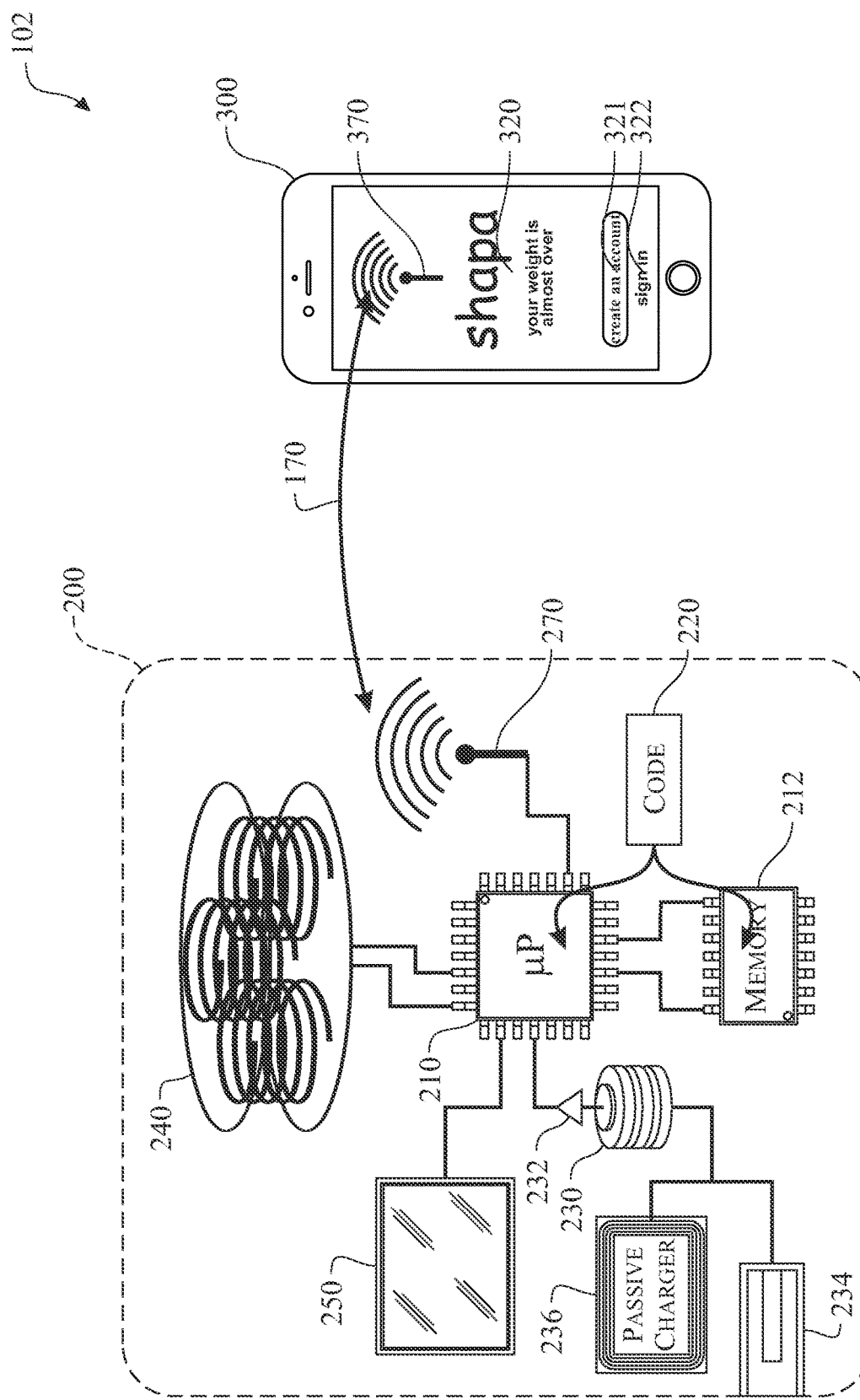
FIG. 3 presents an exemplary schematic diagram introducing a series of exemplary components of a weight management scale employed by the exemplary health and fitness management system originally introduced in FIG. 1.
Figure 4:
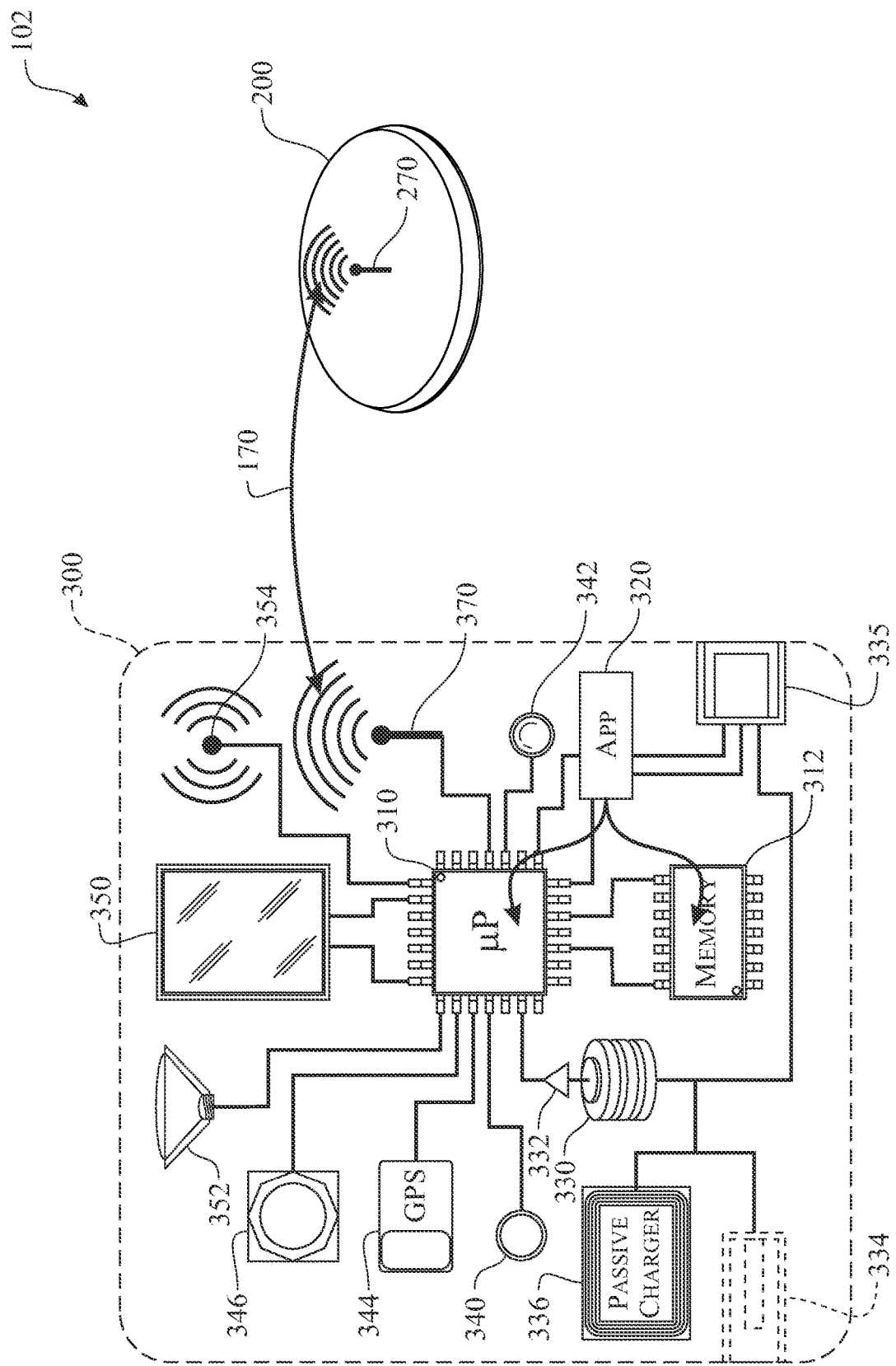
FIG. 4 presents an exemplary schematic diagram introducing a series of exemplary components of a portable computing system employed by the exemplary health and fitness management system originally introduced in FIG. 1.
Figure 5:
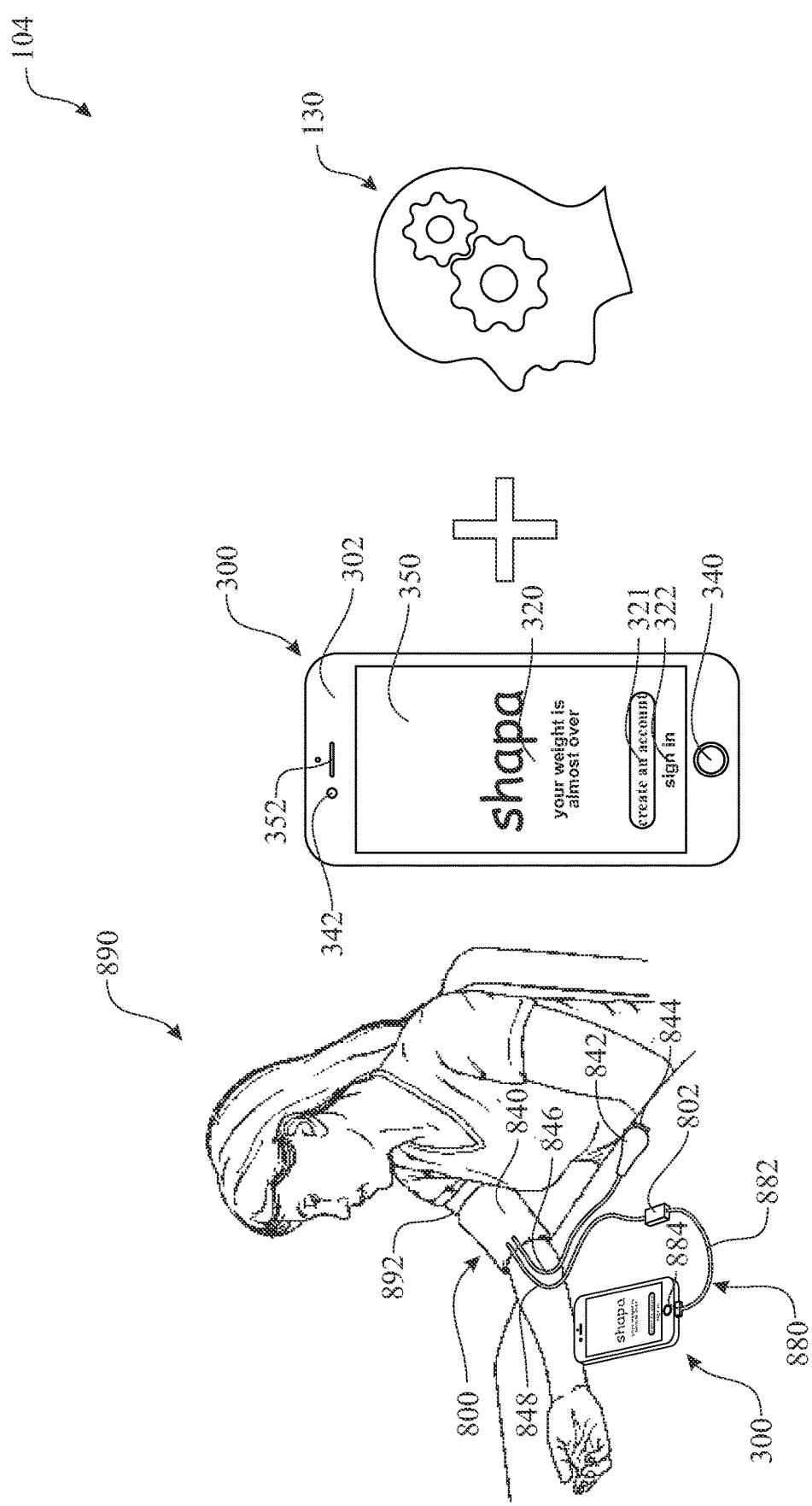
FIG. 5 presents a schematic diagram of second exemplary series of components employed by the exemplary health and fitness management system associated with the operational process flow introduced in FIG. 1.
Figure 6:
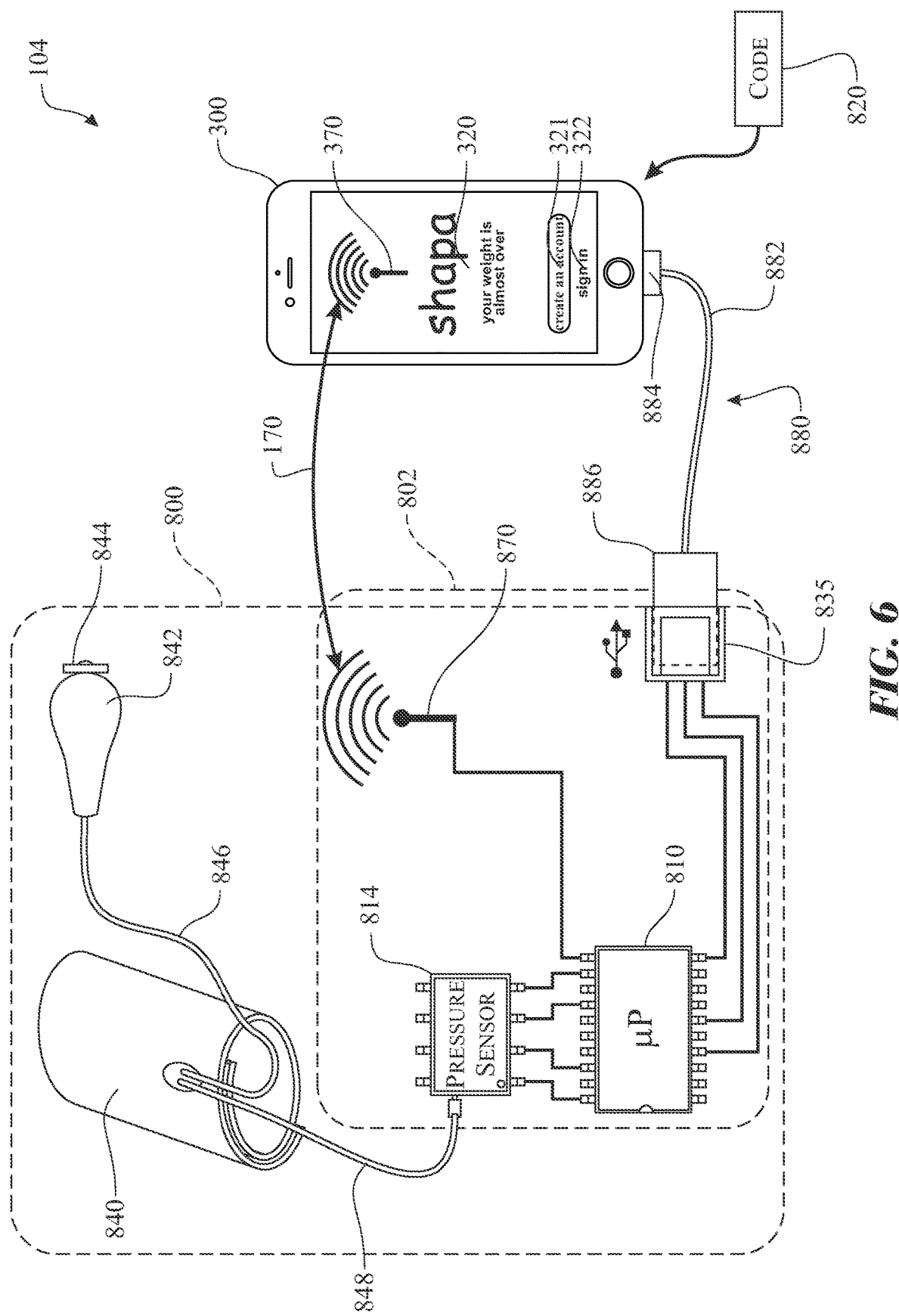
FIG. 6 presents an exemplary schematic diagram introducing a series of exemplary components of a blood pressure acquisition system employed by the exemplary health and fitness management system originally introduced in FIG. 1.
Figure 7:
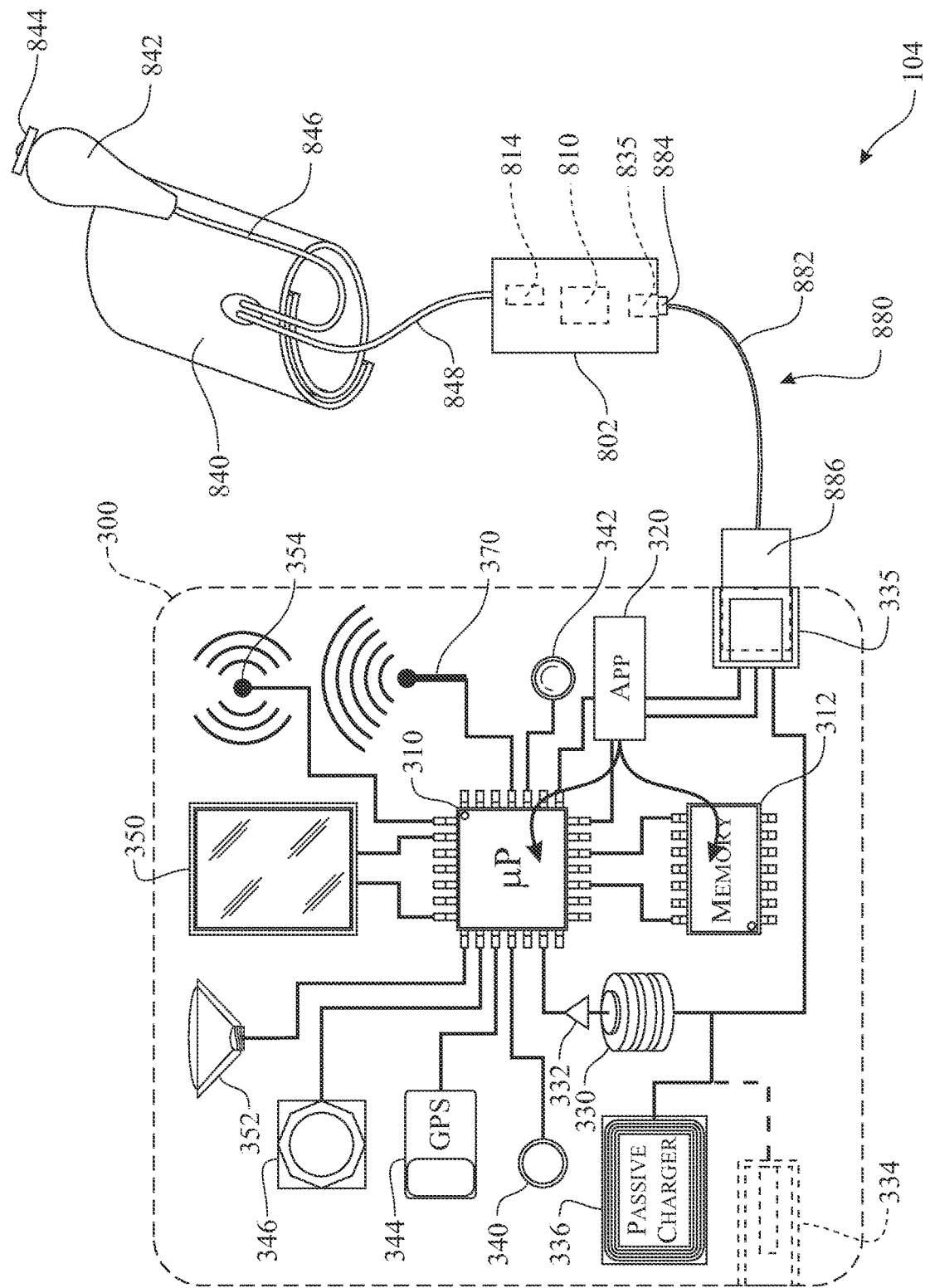
FIG. 7 presents an exemplary schematic diagram introducing a series of exemplary components of the portable computing system adapted for use with the blood pressure acquisition system employed by the exemplary health and fitness management system originally introduced in FIG. 1.
Figure 8:
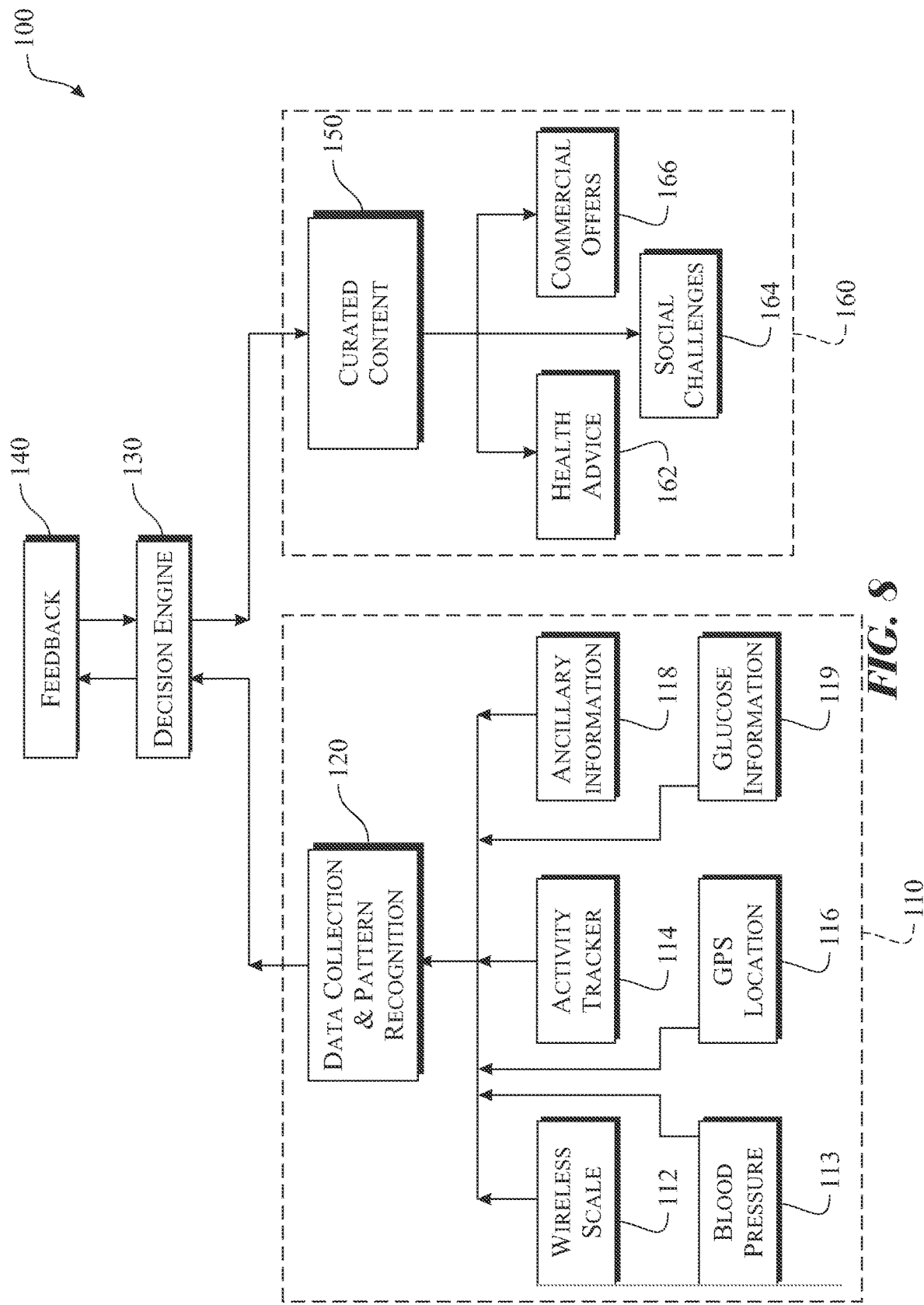
FIG. 8 presents an exemplary flow diagram of the operational process flow of the exemplary health and fitness management system originally introduced in FIG. 1.

An exemplary overview of the process is presented in FIG. 1, with the associated devices of a weight based contributor being presented in FIGS. 2 through 4, the associated devices of a blood pressure based contributor being presented in FIGS. 5 through 7, and a flow diagram being presented in FIG. 8.

A weight management scale 200 is employed to acquire an individual's weight in one exemplary health management system 102. The individual's weight is utilized to determine a health index number, which is presented to the individual. The weight management system 100 relies upon the health index number to avoid presenting a weight measurement 112 to the user. An exemplary schematic diagram of the weight management scale 200 is presented in FIG. 3. The weight management scale 200 includes a weight management scale microprocessor 210, operating in accordance with a weight management scale operating instruction set 220. The weight management scale operating instruction set 220 is commonly stored within a weight management scale non-volatile digital memory 212. The weight management scale non-volatile digital memory 212 is in digital signal communication with the weight management scale microprocessor 210. Electrical power is provided to the weight management scale microprocessor 210 from an external power source, identified as a weight management scale line power input 234 and/or a weight management scale portable power supply 230. The weight management scale portable power supply 230 is preferably rechargeable. The weight management scale portable power supply 230 can be recharged by power from the weight management scale line power input 234, using a weight management scale wireless power charging circuit 236, a solar charger (not illustrated), and the like. A weight management scale power regulator 232 can be integrated into the circuit to provide power management to all of the electrically operated components of the weight management scale 200. A weight acquisition element 240 would be integrated into the weight management scale 200. The weight acquisition element 240 would be in signal communication with the weight management scale microprocessor 210. The weight acquisition element 240 is adapted to acquire a weight of the individual when the individual is properly using the weight management scale 200. The weight acquisition element 240 can be of any suitable electronic weight acquisition device known to those skilled in the art. Information can be provided to the user through a weight management scale display 250, wherein the weight management scale display 250 would be directly or indirectly in signal communication with the weight management scale microprocessor 210. Images can be provided by a display driver (not shown). Information can be conveyed to at least one other computing device, such as a portable computing device 300, by way of a weight management scale wireless communication circuit 270. The weight management scale wireless communication circuit 270 would be in signal communication with the weight management scale microprocessor 210. The weight management scale microprocessor 210 would provide instruction set to the weight management scale wireless communication circuit 270 during a transmission process and receive an instruction set from a received transmission. The weight management scale wireless communication circuit 270 can operate in accordance with any suitable protocol, including Wi-Fi, Bluetooth, Near Field Communication (NFC), Zigbee, and the like. It is also understood that a wired communication protocol, such as Ethernet, and the like can be provided. The components of the weight management scale 200 are enclosed within a weight management scale housing 202. An upper surface of the weight management scale housing 202 can be an upper surface of the weight acquisition element 240, wherein the upper surface of the weight acquisition element 240 would be employed to support the individual while the weight acquisition element 240 acquires the weight 112 of the individual.

A weight management application 320 can operate on the portable computing device 300. Details of the portable computing device 300 are best represented in a schematic diagram illustrated in FIG. 4. The portable computing device 300 can be a Smartphone (as illustrated), a portable computing tablet, a Personal Data Assistant (PDA), a custom portable computing device, and the like. The portable computing device 300 includes a portable computing device microprocessor 310. The weight management application 320 provides an instruction set for operating on the portable computing device microprocessor 310 in conjunction with other instruction sets. The weight management application 320 is commonly stored within a portable computing device non-volatile digital memory 312. The portable computing device non-volatile digital memory 312 is in digital signal communication with the portable computing device microprocessor 310. Electrical power is provided to the portable computing device microprocessor 310 from an external power source, identified as a portable computing device line power input 334 and/or a portable computing device portable power supply 330. The portable computing device portable power supply 330 is commonly rechargeable. The portable computing device portable power supply 330 can be recharged by power from the portable computing device line power input 334 or a Universal Serial Bus (USB) port 335, using a portable computing device wireless power charging circuit 336, using another portable power supply, using a solar charger (not illustrated), and the like. A portable computing device power regulator 332 can be integrated into the circuit to provide power management to all of the electrically operated components of the portable computing device 300. A portable computing device mechanical user input device 340 would be integrated into the portable computing device 300. The portable computing device mechanical user input device 340 would be in signal communication with the portable computing device microprocessor 310. The portable computing device mechanical user input device 340 is adapted to receive inputs from the individual using the portable computing device 300. The portable computing device mechanical user input device 340 can be of any suitable user entry device known to those skilled in the art, such as an electro-mechanical switch, a touchpad or trackpad, a keyboard, a trackball, and the like. The portable computing device 300 can provide output to the user through any of a variety of components. The portable computing device 300 can convey information visually, using a portable computing device display 350, audibly, using a portable computing device speaker 352, motion, using a portable computing device haptic feedback generator 354, and the like. The audio feedback, the visual feedback and the haptic feedback can be operated individually, or in combination with at least one other feedback. The portable computing device display 350 would be directly or indirectly in signal communication with the portable computing device microprocessor 310. Images can be provided by a display driver (not shown). The portable computing device speaker 352 and the portable computing device haptic feedback generator 354 would be operated by a signal from the portable computing device microprocessor 310. A portable computing device camera 342 can be included in the portable computing device 300. The portable computing device camera 342 can be utilized to capture digital still photographs or digital video as desired. The digital still photographs or digital video can be used by the weight management system processing steps 132 to aid in determining the health index number. Other components or circuitry can be integrated into the portable computing device 300 to provide additional information to the portable computing device microprocessor 310 for use with the weight management application 320. For example, a portable computing device Global Position System (GPS) receiver 344 can be integrated into the portable computing device 300. The portable computing device Global Position System (GPS) receiver 344 introduces a capability to acquire location information, movement information, and the like of the portable computing device 300. Similarly, a portable computing device accelerometer 346 can be integrated into the portable computing device 300. The portable computing device accelerometer 346 introduces a capability to different movement information, and the like of the portable computing device 300. The movement information acquired using the portable computing device Global Position System (GPS) receiver 344 and/or the portable computing device accelerometer 346 can be related to a user's activities. The acquired movement information can be used by the weight management application 320 for maintaining a history of the activities of the user.

The portable computing device 300 can communicate with external devices using any suitable wired and/or wireless communication circuits and protocols. In the exemplary illustration, the portable computing device 300 includes each of a wired communication circuit (a Universal Serial Bus (USB) port 335) and a portable computing device wireless communication circuit 370. The Universal Serial Bus (USB) port 335 can additionally be utilized to convey signal or data information.

Information can be between the portable computing device 300 and at least one other device comprising a transceiver operating in accordance with a like protocol, such as the weight management scale wireless communication circuit 270 of the weight management scale 200, by way of a wireless communication link 170. The portable computing device wireless communication circuit 370 would be in signal communication with the portable computing device microprocessor 310. The portable computing device microprocessor 310 would provide instruction set to the portable computing device wireless communication circuit 370 during a transmission process and receive an instruction set from a received transmission. The portable computing device wireless communication circuit 370 can operate in accordance with any suitable protocol, including Wi-Fi, Bluetooth, Near Field Communication (NFC), Zigbee, and the like. It is also understood that a wired communication protocol, such as Ethernet, and the like can be provided. The components of the portable computing device 300 are enclosed within a portable computing device housing 302.

The weight management system 100 collects weight management system baseline data 110 from a series of data collection sources, including an individual's age, an individual's weight, an environment, context, a diet, exercise habits, sleep habits, daily routines, social network entries, labs and medical history, genome, and the like. At least a portion of the data weight management system baseline data 110 can be collected using the weight management application 320 in conjunction with the data collection components 344, 346 of the portable computing device 300. Data 110 can be collected using a weight management scale 200, a portable computing device 300 operating in accordance with instructions from a weight management application 320, and an intelligent behavioral platform that profiles the individual and recommends behavioral and diet modifications. The weight management scale 200 is designed to collect a digital representation of a weight of the individual, while not disclosing the acquired weight to the individual. Additional data can be collected using other devices, such as a Global Positioning System (GPS) 344, a beacon locating system (an application in conjunction with the portable computing device wireless communication circuit 370), a pedometer (using the portable computing device accelerometer 346), and the like.

The data 110 acquired by each data collection device 200, 344, 346, etc. can be stored within the data acquisition device, such as the weight management scale 200, or transferred to a data collection device, such as a portable computing device 300. The data 110 could be uploaded to the portable computing device 300 using wired (such as Ethernet) or wireless technology (such as the weight management scale wireless communication circuit 270 and the portable computing device wireless communication circuit 370). The collected data 110 would eventually be transferred to the portable computing device 300 operating the associated software or application 320.

The collected data 110 can be utilized by the application 320 to determine any of a number of data points (step 120). Collected data 110 can include weight information collected from the weight management scale 200 (wireless scale acquired information 112), blood pressure and heart rate information collected from the blood pressure acquisition system 800 (blood pressure and/or heart rate information 113), activity information (collected from any suitable activity acquisition device, such as the portable computing device 300; an activity tracker 114 (commonly described as a wireless-enabled wearable technology devices that measure data such as the number of steps walked, heart rate, quality of sleep, steps climbed, and other personal metrics); a global positioning System (GPS) location 116 (acquired using a Global Positioning System (GPS) receiver, a beacon locating system, and the like.); and any other ancillary information 118 (collected from a respective data acquisition device, application (such as a calendar, an activities list, social media, and the like), blood sugar levels acquired using a glucose monitor (such as the 1000) or manually entered by the user). One example would be the use of the GPS information 116 and/or beacon information to determine locations associated therewith, such as restaurants, gyms, stores, and the like. The weight management system 100 can additionally determine the span of time the individual remains at the specific location. Effectively, the weight management system 100 is collecting a geographic history of locations visited by the individual, time spent at each associated geographic location, and the like.

The weight management system 100 collects information associated with travel and activity history through social media activities.

Other devices that can be employed by the system include those to collect one or more vital signs of the individual, including temperature, heart rate, blood pressure, and the like. The collected data 110 would also be collected and forwarded to the application 320, while not disclosing the acquired data points to the individual.

The system can be adapted to monitor the user 890 for chronic heart failure. The system would utilize the data acquired from the weight management scale 200 to determine potential for and/or risks of chronic heart failure. The system can utilize the trends of the blood pressure rates to determine potential for and/or risks of chronic heart failure.

The system can include a Congestive Heart Failure (CHF) monitoring feature. The Congestive Heart Failure (CHF) monitoring feature allows for improved remote monitoring of patients living with and managing congestive heart failure on an outpatient basis. The Congestive Heart Failure (CHF) monitoring feature allows the healthcare provider and user to more closely monitor for weight fluctuations that would warrant a change in the care plan of the user. The user will use the weight management scale 200 at least daily to acquire the user's weight, which is transferred to the application. The backend system will monitor the weight trends for the user and specifically monitor for sudden weight gain over a predetermined number of consecutive days. One exemplary threshold for weight gain and duration of days is set to a default established by the American College of Cardiology guidelines. The application can enable customization of the thresholds by the care provider, the user, or any other allowed party, if they have specific thresholds for users or groups of patients. When the system detects a weight gain that exceeds the threshold set for pounds/kilograms and time frame the system will prompt the user to repeat the weigh-in measurement process for confirmation. The system will also display prompts in the application to ensure that there are no external factors that may contribute to the weight gain (i.e. heavier clothing, etc). If the weight gain is confirmed, the user will be notified of the weight gain in pounds/kilograms and the duration of days gained is noted. The user would also be encouraged to contact their healthcare provider for further instructions.

The user will have access to application's five (5) point color scale and the Age feedback mechanism in the application experience that are driven by the backend.

The system also has an administrator portal that the health care management team can access to view which users under their care have had measurements outside the threshold to more efficiently triage who might need closer flow up and support.

The systems Congestive Heart Failure program also leverages artificial intelligence to reinforce diet and lifestyle education and behaviors that support management of life with Congestive Heart Failure (CHF). This education is delivered through missions and content in the application. The information is personalized to the user, based in-part, to their responses to the on-boarding assessment questionnaire completed upon sign up in the app. The user will also have access to customizable reminders and nudges delivered by the system to complete activities in the application and be consistent with the daily weigh-in action.

A second example is presented in FIGS. 5, 6, and 7, which introduces a health management system 104 using a blood pressure acquisition system 800. The blood pressure acquisition system 800 and the weight acquisition system 200 are adapted for use with the portable computing device 300 in a similar manner. The distinction is that the portable computing device 300 is adapted for use with the blood pressure acquisition system 800 in the exemplary embodiment, whereas the portable computing device 300 is adapted for use with the weight acquisition system 200 in the previous example.

The illustrations in FIGS. 5, 6, and 7 introduce details associated with the blood pressure acquisition system 800 and how the portable computing device 300 is adapted for use with the blood pressure acquisition system 800. The blood pressure acquisition system 800 includes a blood pressure acquisition element (pressure cuff) 840. The blood pressure acquisition element (pressure cuff) 840 is placed around an upper arm 892 of a user 890, as illustrated in FIG. 5. A pressure generator 842 generates and provides pressure to the blood pressure acquisition element (pressure cuff) 840 through a pressure control transfer tube 846. A pressure relief control 844 releases pressure from the blood pressure acquisition element (pressure cuff) 840 in a controlled manner. The pressure generator 842 and pressure relief control 844 can be manually operated, as shown, or automated. Each arrangement is well known by those skilled in the art. A pressure sensor 814 is in pneumatic communication with the blood pressure acquisition element (pressure cuff) 840 via a pressure output transfer tube 848. The pressure sensor 814 monitors changes in pressure of the blood pressure acquisition element (pressure cuff) 840 to determine the blood pressure of the monitored user 890. The pressure sensor 814 converts the pressure received through the pressure output transfer tube 848 to an electrical signal. Operation of the blood pressure acquisition system 800 is provided by a blood pressure acquisition system microprocessor 810. The blood pressure acquisition system microprocessor 810 is in signal communication with the pressure sensor 814. The blood pressure acquisition system microprocessor 810 provides operational control to the pressure sensor 814 and receives an acquired signal from the pressure sensor 814. A blood pressure acquisition system connector 835 provides two purposes: (1) the blood pressure acquisition system connector 835 provides a signal interface between the blood pressure acquisition system microprocessor 810 and external devices and (2) a source of electrical power can be obtained through a blood pressure acquisition system connector 835. It is also recognized that the circuitry can be powered by a portable power supply, similar to the weight management scale portable power supply 230 of the weight management scale 200. The blood pressure acquisition system microprocessor 810, the pressure sensor 814, and the blood pressure acquisition system connector 835 can be integrated into a blood pressure acquisition system electronics assembly housing 802. When viewed, the blood pressure acquisition system electronics assembly housing 802 is representative of the assembly.

The blood pressure acquisition system 800 can be arranged to communicate with the portable computing device 300 via a wired communication link or a wireless communication link 170. In a wired communication arrangement (as illustrated in FIGS. 6 and 7), a communication cable assembly 880 provides a disconnectable wired connection between the blood pressure acquisition system 800 and the portable computing device 300. The communication cable assembly 880 can include a blood pressure acquisition element (pressure cuff) 840 provided in electro-mechanical assembly at a first end of a communication cable 882 and a communication cable second end connector 886 provided in electro-mechanical assembly at a second end of the communication cable 882. The communication cable first end connector 884 would be inserted into a blood pressure acquisition system connector 835 of the blood pressure acquisition system 800 and the communication cable second end connector 886 would be inserted into the Universal Serial Bus (USB) port 335 of the portable computing device 300. The mechanical configuration of the communication cable first end connector 884 would be such to electro-mechanically couple with the blood pressure acquisition system connector 835 and the mechanical configuration of the communication cable second end connector 886 would be such to electro-mechanically couple with the Universal Serial Bus (USB) port 335. The electro-mechanical configuration of the communication cable first end connector 884 can be similar to the electro-mechanical configuration of the communication cable second end connector 886 or the electro-mechanical configuration of the communication cable first end connector 884 can be distinct from the electro-mechanical configuration of the communication cable second end connector 886.

In the exemplary arrangement, the peripheral hardware design contains just enough elements to transmit the pressure signal to a mobile phone for the digital signal processing.

In a wireless arrangement, the blood pressure acquisition system 800 can include a blood pressure acquisition wireless communication circuit 870, where the blood pressure acquisition wireless communication circuit 870 would provide the functions enabling the wireless communication link 170.

The blood pressure acquisition wireless communication circuit 870 can be wired by the optional portable power supply, thus providing a completely wireless link between the blood pressure acquisition system 800 and the portable computing device 300.

Details in determining the blood pressure are provided by the portable computing device 300. A blood pressure acquisition operating instruction set 820 is installed onto the portable computing device 300, such as in a form of an application. The application running on the portable computing device 300 provides the majority of the operating horsepower for the blood pressure acquisition system 800.

Blood pressure measurements of a user 890 are filtered so that the blood pressure acquisition system 800 only considers measurements that appear to be valid. The blood pressure acquisition system 800 looks for any measurements that appear to be statistically invalid, for example, due to device error.

The results of the blood pressure acquisition system 800 (or any other medical characteristic measurement or combination of measurements) can be presented in a form of a number similar to the weight process (as previously described), a color, or any other suitable reference. Examples of color displays are presented in FIGS. 13 and 14.

Figure 13:
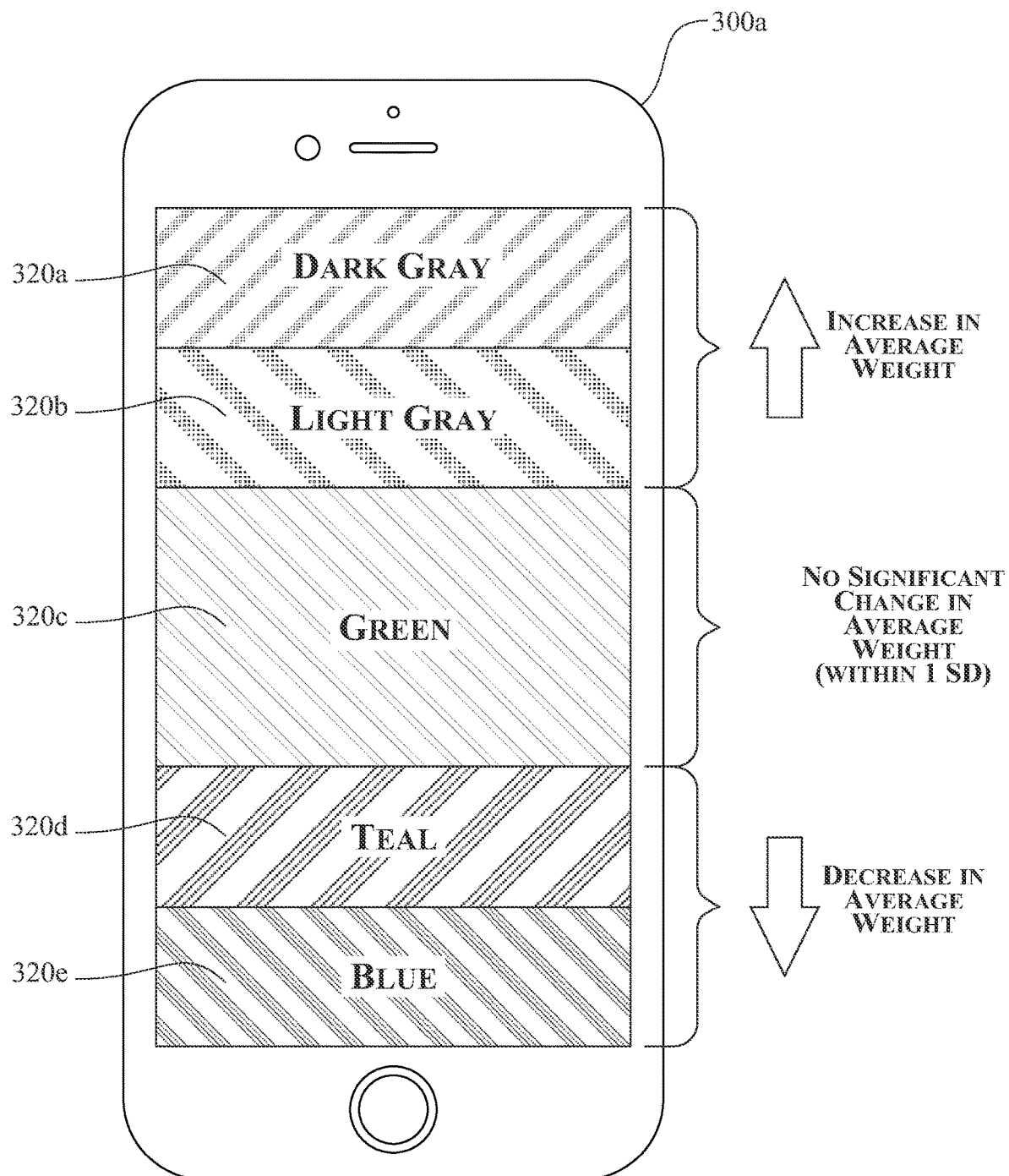
FIG. 13 presents a plan view of the exemplary portable computing device (Smartphone), wherein the exemplary portable computing device is displaying an index of different exemplary colors representative of a status of a user's health.

Since the system can offer user health and fitness feedback in a form of a color rating, the system can display a color index, as illustrated in FIG. 13.

An exemplary color index is shown in a portable computing device having a color index display 300a. The exemplary color index displays five (5) exemplary colors for presenting various degrees of health and fitness status.

The illustrated five (5) exemplary colors are as follows:
A first color (Dark gray) 320a
A second color (Light gray) 320b
A third color (Green) 320c
A fourth color (Teal) 320d
A fifth color (Blue) 320e

Figure 14:
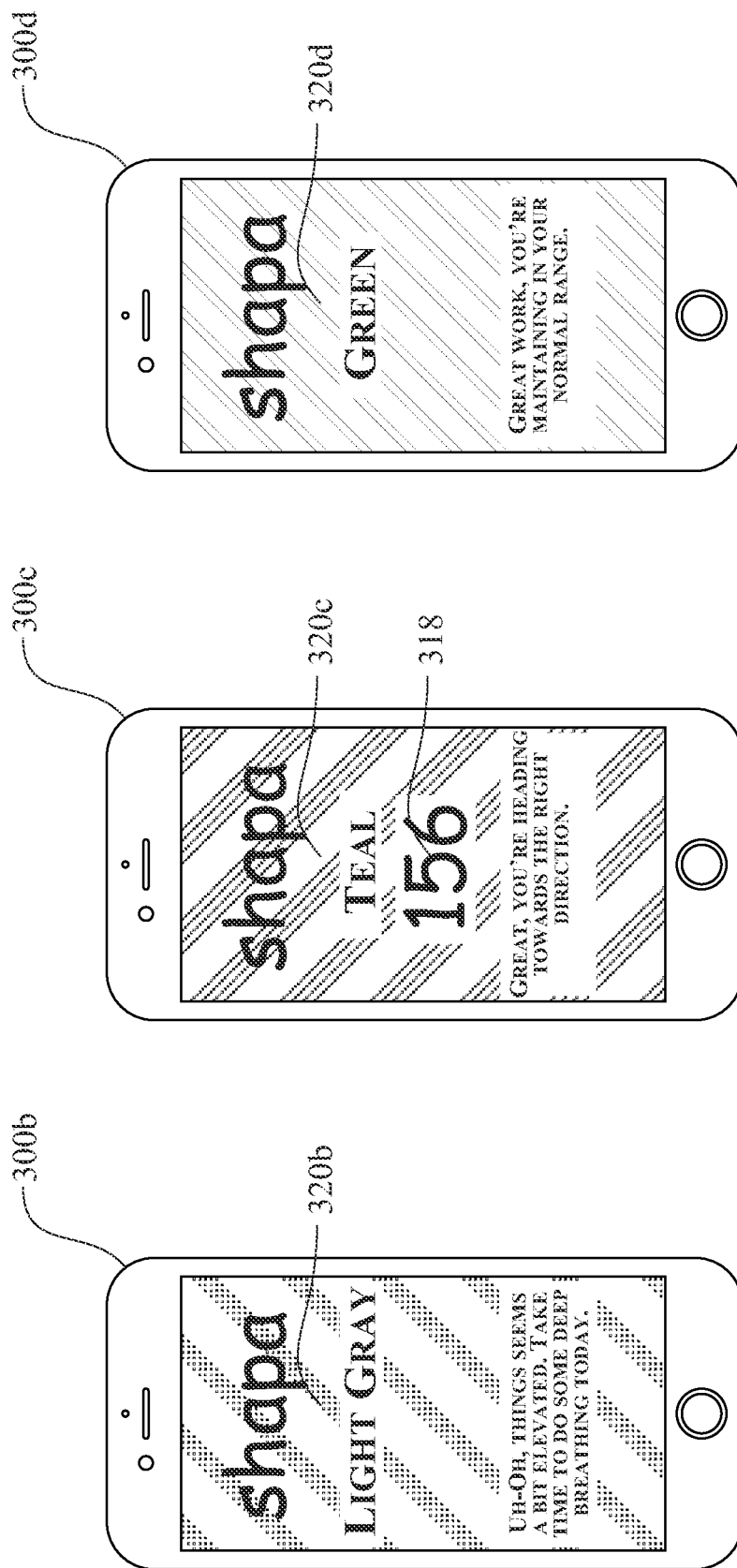
FIG. 14 presents a plan view of exemplary portable computing devices (Smartphones), each exemplary portable computing device displaying a different exemplary color representative of a status of a user's health.
Figure 15:
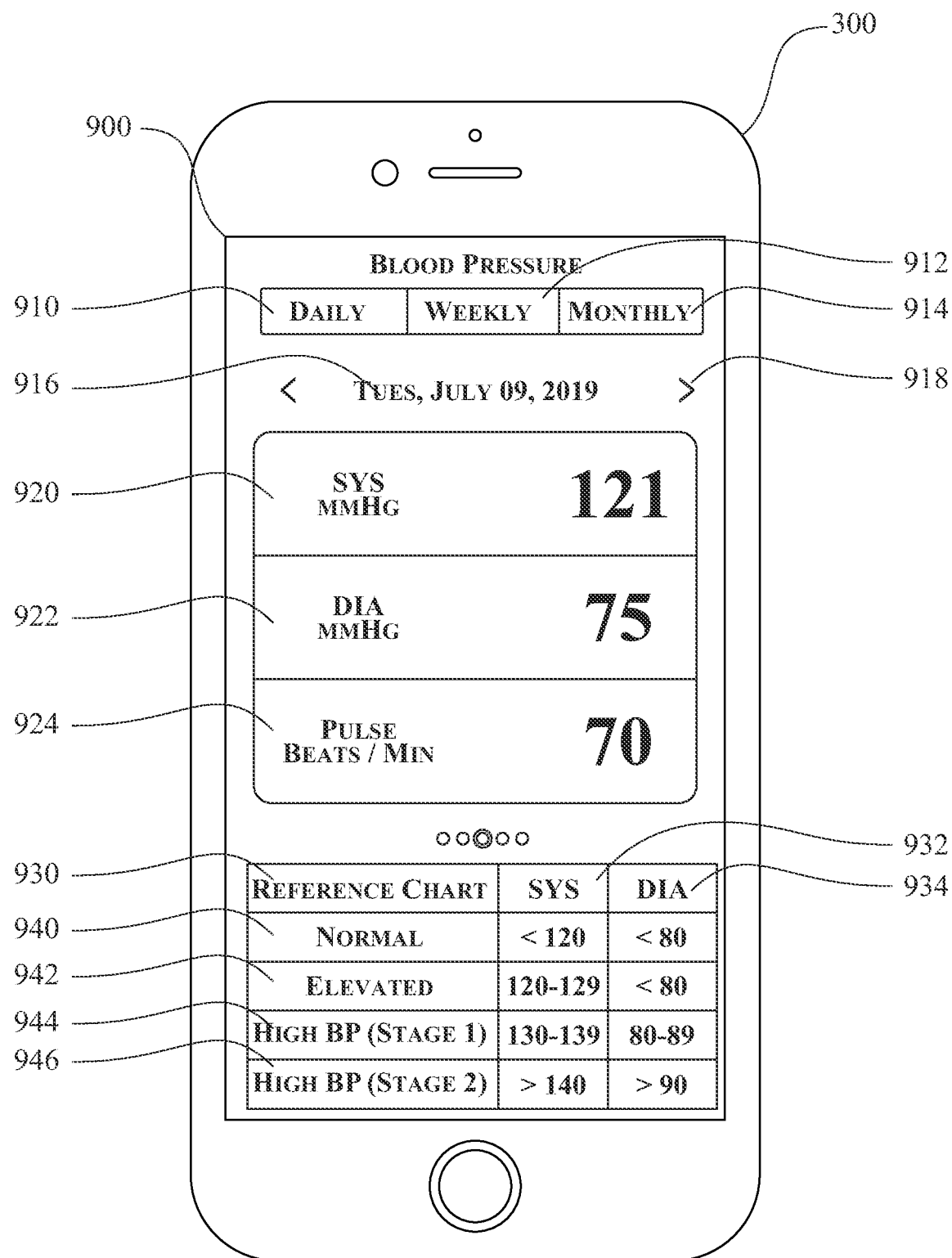
FIG. 15 presents a plan view of an exemplary portable computing device (Smartphone) displaying a data associated with the acquired blood pressure and a reference chart for interpreting the displayed measurements.

Examples of an output are presented in FIG. 14, wherein:

An exemplary second color display 320b is shown in a portable computing device having a second exemplary color state display 300b. The exemplary second color is light gray, where light gray indicates that improvements are still desired.

An exemplary third color display 320c is shown in a portable computing device having a third exemplary color state display 300c. The exemplary third color is teal, where teal indicates a trend in a direction towards a normal or desired range. This exemplary drawing illustrates a scenario where the application is configured to display both a color and a health index number 318.

An exemplary fourth color display 320d is shown in a portable computing device having a fourth exemplary color state display 300d. The exemplary fourth color is green, where green indicates a level or reading that is within the normal or desired range.

The display can include a text description of the color to ensure the interpretation of the color is correct. This would also address those who are color blind. The color (and any other data) can also be presented in audio format for user's that are sight impaired.

The blood pressure acquisition system 800 can use the following algorithm to calculate the user's statistical z-score:

$$\text{z-score} = (\text{Latest\_Blood\_Pressure} - \text{mean})/\text{std\_dev}$$

Where:
Latest_Blood_Pressure=The average of the user's last 10 measurements
mean=The mean of the user's last 30 measurements
std_dev=The standard deviation of the user's last 30 measurements The z-score calculation above is then mapped to a representative color in accordance with the following:

$$\text{z-score} < -1.0 \Rightarrow \text{BLUE}$$

$$-1.0 \le \text{z-score} < -0.5 \Rightarrow \text{TEAL}$$

$$-0.5 \le \text{z-score} < 0.5 \Rightarrow \text{GREEN}$$

$$0.5 \le \text{z-score} < 1.0 \Rightarrow \text{GRAY}$$

$$\text{z-score} \ge 1.0 \Rightarrow \text{DARK GRAY}$$

The color representation can also be applied to a user's weight.

First, a user's measurements are filtered so that the blood pressure acquisition system 800 considers only AM (morning) measurements for use in the algorithm. The blood pressure acquisition system 800 also filters out any measurements that appear to be invalid; for example, due to a scale error or a user error such as using the scale on carpeting.

The system can use the following algorithm to calculate the user's statistical z-score:

$$\text{z-score} = (\text{Latest\_Weight} - \text{mean})/\text{std\_dev}$$

Where:
Latest_Weight=The average of the user's last 6 measurements
mean=The mean of the user's last 20 measurements
std_dev=The standard deviation of the user's last 20 measurements When using a color, the z-score calculation above is then mapped to a respective color such as by the following example:

$$\text{z-score} < -1.0 \Rightarrow \text{BLUE}$$

$$-1.0 \le \text{z-score} < -0.5 \Rightarrow \text{TEAL}$$

$$-0.5 \le \text{z-score} < 0.5 \Rightarrow \text{GREEN}$$

$$0.5 \le \text{z-score} < 1.0 \Rightarrow \text{GRAY}$$

$$\text{z-score} \ge 1.0 \Rightarrow \text{DARK GRAY}$$

Blood pressure cuff 840: The blood pressure cuff 840 has the ability to display the blood pressure values or not to display the blood pressure values. If the patient's result is above the average measurement than the number will appear on the screen. If not the representative color will appear on the portable computing device 300.

The blood pressure acquisition system 800 will show progressive milestones based on the user's health improvement. For example, if a user's health improves, the user 890 can do more at walking, sleep better, have more/better sex, and the like.

The blood pressure acquisition system 800 can also be used to determine a heart rate of the user 890.

The above presents a process for informing a user of a trend or health status without providing a quantitative value that the user can associate directly with. There are benefits associated with not providing the quantitative values to the user. In an alternative mode, the acquired data, in a format of quantitative values, can be presented to the user, as illustrated in FIG. 14, wherein a blood pressure output display 900 is presented on an exemplary portable computing device 300. The blood pressure output display 900 includes user selectable options, including a range of time for display and the associated quantitative values acquired. More specifically, the range of time for display can include a daily view selection 910, a weekly view selection 912, and a monthly view selection 914. It is understood that the range of time for display can be any suitable range, including those illustrated, hourly, bi-weekly, bi-monthly, annually, and the like. The selected range can be displayed to the user. In the exemplary illustration, the range of time selected is the daily view selection 910. The user can then scroll to the desired date associated with the daily view selection 910. The selected date is presented as a date display 916. The user can contact or select the respective date incrementing scroll icon 918 to increment the selection in an increasing or decreasing direction. The user can select the date incrementing scroll icon 918 on the right to increase the date for viewing. Similarly, the user can select the date incrementing scroll icon 918 on the left to decrease the date for viewing. When the user selects a range (such as the weekly view selection 912 or the monthly view selection 914), the date display 916 would display the first date and the last date of the range.

Once the range of time for display is established by the user, the blood pressure output display 900 displays the respective information. In the exemplary illustration, the blood pressure output display 900 is presenting a systolic (sys) pressure 920, a diastolic (dia) pressure 922, and a heart beat rate 924 in a numerical format. The presented systolic (sys) pressure 920, diastolic (dia) pressure 922, and heart beat rate 924 are those that were recorded on Tuesday, Jul. 09, 2019. The displayed information can be a daily average, the first recorded information on that date, the last recorded information on that date, the highest recorded information on that date, the lowest recorded information on that date, or any other variant. The variant can be established by the system, established by the user, or changeable.

The blood pressure output display 900 can include a reference chart 930 to provide guidance to the user. The reference chart 930 can be presented in table format, including reference to a systolic (sys) pressure in a systolic (sys) pressure column 932 and a diastolic (dia) pressure in a diastolic (dia) pressure column 934 for each of a normal blood pressure level reference 940, an elevated blood pressure level reference 942, a high blood pressure level (stage 1) reference 944, a high blood pressure level (stage 2) reference 946, and the like. The reference chart 930 can also include reference to ranges for heart rates (not shown).

The exemplary illustration presents the quantitative values in text format. The quantitative values can also be presented in a chart format or any other suitable format for displaying the quantitative values.

The weight management system 100 collects the available acquired information from the various sources and analyzes the collected information 110 within a decision engine 130. The decision engine 130 optimizes feedback and forwards the feedback or curated content 150 to the individual. This can include health advice 162, social challenges 164, and commercial offers 166 (to provide incentives to the individual). The weight management system processing 130 can include a learning function, which is a component of weight management system processing steps 132. The weight management system processing steps 132 would include any steps for learning, improving, processing, recommending, and nudging to continuously improve the overall process. This is accomplished at least in part by using a feedback loop 140, wherein the feedback loop 140 would compare data acquired prior to disclosing weight management system recommended actions 160 with data acquired following the disclosure of the weight management system recommended actions 160.

Figure 9:
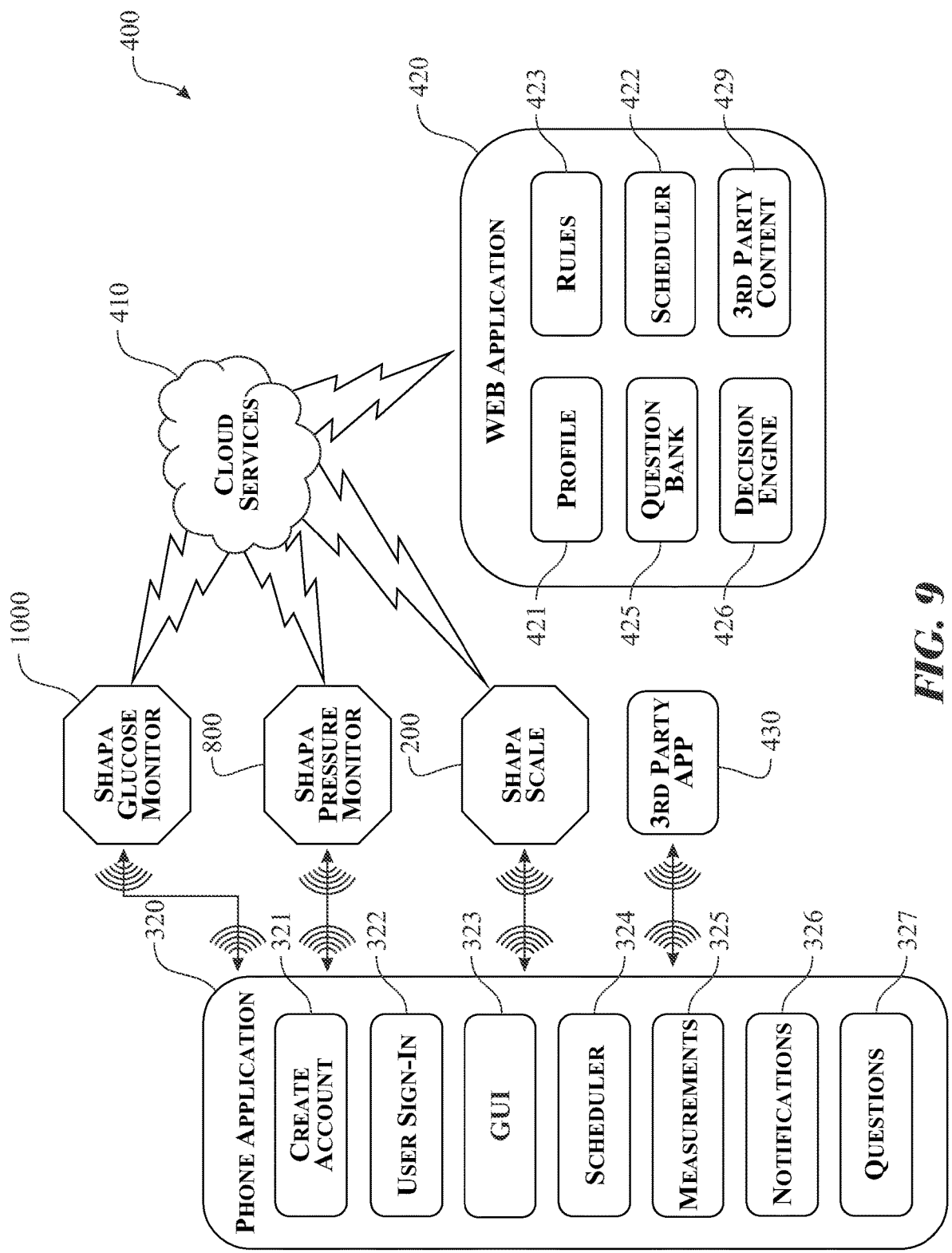
FIG. 9 presents an exemplary flow diagram detailing the function of the data collection and pattern recognition and decision engine of FIG. 8.

Details of the data collection and pattern recognition 120 and decision engine 130 are presented in an exemplary flow diagram illustrated in FIG. 8. The diagram illustrated in FIG. 9 shows how the health and fitness management system application will interact with the system's own server 420 and third parties application 430 using a weight management system network 400. The health and fitness management system 100 will also interact with a cloud based system 410 in order to store and protect the user's data.

The weight management application 320 operates in accordance with a user account. The user can create an account by selecting a user account creation icon 321. The user would provide a user identification and an associated user password. The user account creation process can include steps for acquiring additional information, such as age, height, current weight, target weight, social networking accounts, calendar access, location access, medical records access and the like. Once the user account is created, the user can access the account by selecting a user account log in icon 322 and providing the requested information, such as a user identification and an associated user password. The weight management application 320 can provide a number of features to collect the desired data 110 and present information to the user. Examples shown in the exemplary embodiment include a weight management application Graphical User Interface (GUI) 323, a weight management application scheduler 324, a weight management application measurement 325, a weight management application notification 326, weight management application questions 327, and the like.

Data can be acquired from other sources, such as the weight management scale 200, a weight management third-party application 430, a blood pressure monitor 800, a glucose monitor 1000, and the like. The weight management application 320 can operate independently or in conjunction with a web-based application 420. In the exemplary schematic illustrated in FIG. 9, the weight management system network 400 employs a web-based application 420. In an alternative configuration, the weight management application 320 can operate independently and would incorporate the functionality of the exemplary web-based application 420.

Data weight management system baseline data 110 can be transferred between the weight management application 320 and the web-based application 420 directly or indirectly, such as through a weight management system network non-volatile remote services 410. Information acquired by the weight management scale 200 can be transferred to the weight management system network non-volatile remote services 410 for use by the web-based application 420. The web-based application 420 can include a number of features. The exemplary web-based application 420 includes a user profile 421, a user scheduler 422, a set of weight management system rules 423, a weight management questions bank 425, a weight management decision engine 426, and capability of using weight management third-party content 429. An exemplary series of questions that can be included within the weight management questions bank 425 is provided near the end of this disclosure.

The user profile 421 acquires, retains and updates a profile of the account user.

The weight management questions bank 425 contains a series of questions to obtain and collect information from the user. The series of questions included in the weight management questions bank 425 are directed to aid the weight management decision engine 426 in determining suggested changes to the user's activities, environment, routines, eating habits, and the like. Essentially, the exemplary weight management decision engine 426 provides the functionality of the weight management system processing 130 described above. The weight management decision engine 426 can utilize the weight management system rules 423 in conjunction with data collected using the weight management questions bank 425 as well as data collected by the weight management application 320 to provide the suggested changes. The weight management decision engine 426 can additionally consider information collected through weight management third-party content 429 when determining suggested guidance to the user. The weight management decision engine 426 would utilize historical information acquired over time, including weight measurements 325, user activities, and the like. Details are provided below.

The web-based application 420 provides a communication system between the weight management application 320 operating on the portable computing device 300, the weight management scale 200, weight management system network non-volatile remote services 410, and a web-based application 420. One or more weight management third-party applications 430 can be included, wherein the weight management third-party application 430 can reside and operate on the weight management application 320 or reside and/or operate on a different computing device, such as a server, a different computer, and the like.

Figure 12:
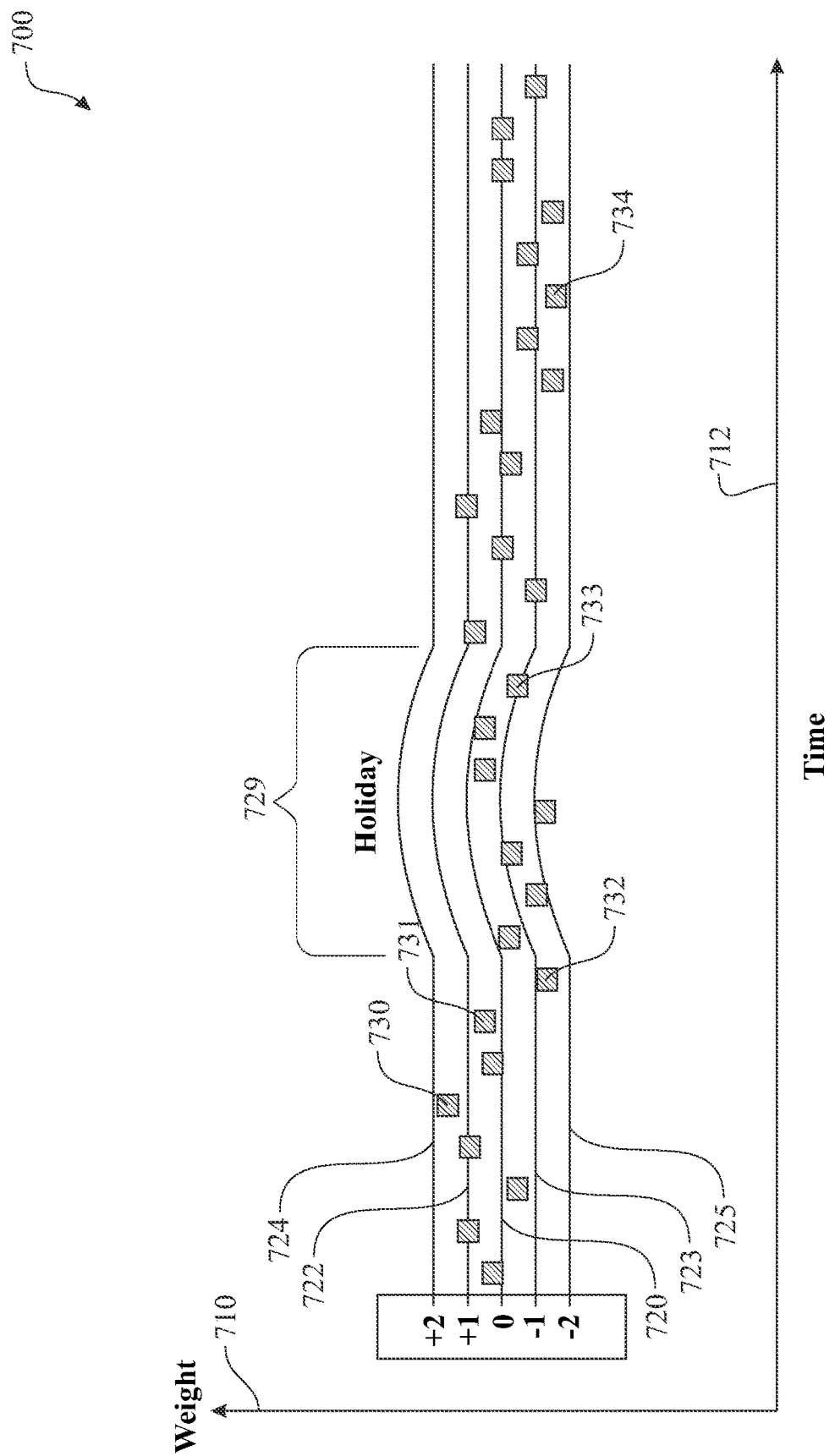
FIG. 12 presents fluctuations of an exemplary health index number presented within a series of Bollinger Bands, wherein the chart illustrates an exemplary scenario including effects of a holiday.

The weight management system 100 utilizes constant feedback to determine improvements in the individual's health and fitness. The feedback additionally information the system of suggestions that are working and those suggestions that do not appear to be working. The feedback can be correlated to certain events or a period of time considered to be an anomaly, such as holidays referenced by a holiday time band 729 (as shown in FIG. 12).

The system can be adapted to provide feedback at specific times and/or locations. For example, the portable computing device 300 would include a GPS system 344, which would notify the Application 320 of a location of the individual. For example, this feature can inform the Application 320 that the individual is at a restaurant, wherein the Application 320 would respond by presenting a recommendation for an entree. The Application 320 can go farther by recommending a different restaurant. Conversely, the Application 320 can recognize a lunch time and present a suggested location and menu for the individual for lunch.

The weight management system 100 would monitor the activities of the individual to determine any changes in the environment, activities, habits, and the like and optimize the health and fitness plans accordingly.

The system additionally utilizes a health index number.

The system collects the following information to determine the health index number:
Individual's Current Age [Age(C)]
Individual's Ideal Age [Age(I)]
Individual's Starting or Initial Weight [Weight(S)]
Individual's Current Weight [Weight(C)]
Individual's Ideal Weight [Weight(I)]

The system utilizes the collected information to determine an effective loss in age, wherein the effective loss in age is calculated using an effective loss in age equation of:

$$\text{Effective Loss In Age} = \frac{[\text{Weight}(S) - \text{Weight}(C)]}{[\text{Weight}(S) - \text{Weight}(I)]} * [(\text{Age}(C) * \text{factor}) - \text{Age}(I)]$$

The system utilizes the collected information to determine the health index number, wherein the health index number is calculated using a health index number equation of:

$$\text{Health Index Number} = \text{Age}(C) - \frac{[\text{Weight}(S) - \text{Weight}(C)]}{[\text{Weight}(S) - \text{Weight}(I)]} * [(\text{Age}(C) * \text{factor}) - \text{Age}(I)]$$

Figure 10:
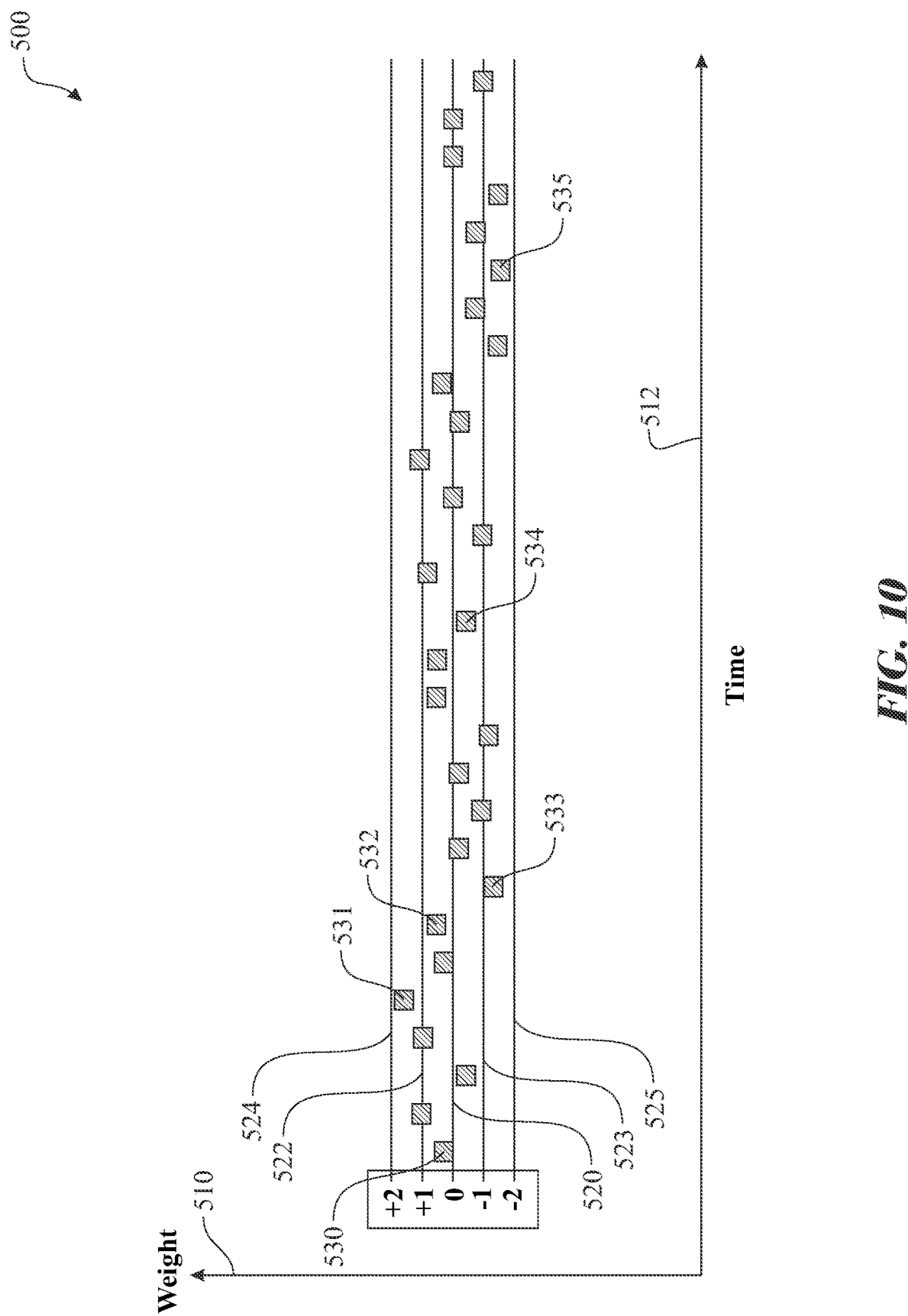
FIG. 10 presents fluctuations of an exemplary health index number presented within a series of Bollinger Bands, wherein the chart illustrates an exemplary baseline of the individual's overall health.
Figure 11:
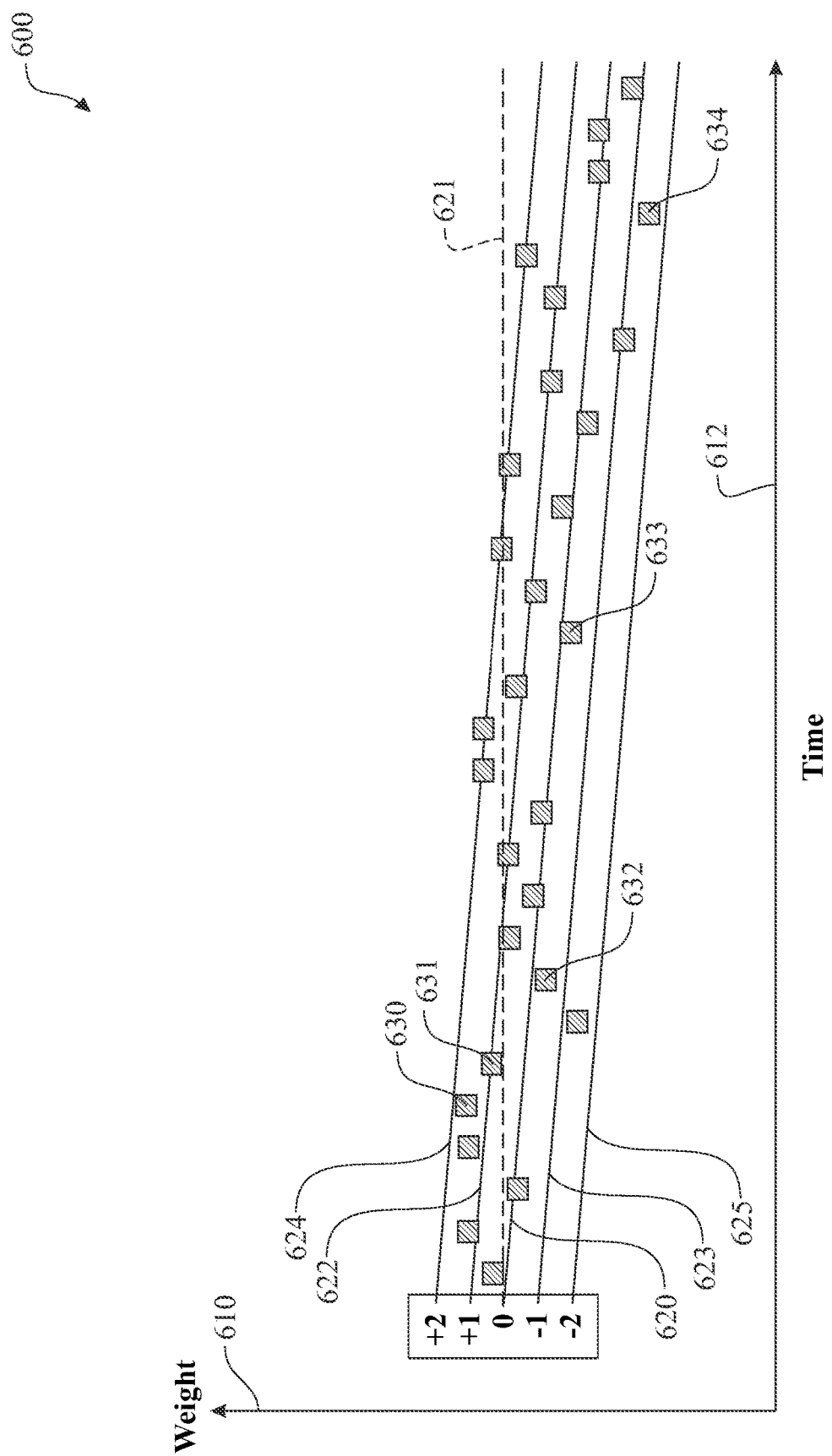
FIG. 11 presents fluctuations of an exemplary health index number presented within a series of Bollinger Bands, wherein the chart illustrates an exemplary improvement in the individual's overall health.

The health index number can be charted within Bollinger Bands, as illustrated in FIGS. 10 through 12.

Bollinger bands were introduced by John Bollinger as new indicators. Bollinger bands are an interesting tool because one sees the channel or band of their weight history (and the individual can define the moving average period and even whether it is a simple or exponential moving average). The individual can also define the upper and lower band distance by using standard deviation (and the number used here could relate to "just noticeable differences").

There are 3 indicators: Bandwidth, BBImpulse, and percent bandwidth (%b).

BBImpulse measures price change as a function of the bands; percent bandwidth (%b), which normalizes the width of the bands over time; and bandwidth delta, which quantifies the changing width of the bands.

The percent bandwidth (%b) (pronounced "percent b") is derived from the formula for Stochastics and shows where price is in relation to the bands. %b equals 1 at the upper band and 0 at the lower band. Writing "upperBB" for the upper Bollinger Band, "lowerBB" for the lower Bollinger Band, and "last" for the last (price) value:

%b=(last-lowerBB)/(upperBB-lowerBB)

Bandwidth indicates how wide the Bollinger Bands are on a normalized basis. Writing the same symbols as before, and "middleBB" for the moving average, or middle Bollinger Band:

Bandwidth=(upperBB-lowerBB)/middleBB

Using the default parameters of a 20-period look back and plus/minus two standard deviations, bandwidth is equal to four times the 20-period coefficient of variation.

Uses for %b include system building and pattern recognition. Uses for bandwidth include identification of opportunities arising from relative extremes in volatility and trend identification.

This means that increases in bandwidth would be expected with holidays or illness. The %b is a great metric for a single number that tells an individual "relative" to their range, are they low, medium, high.

BBImpulse appears to help identify degree of change, relative to oneself and their history.

Bollinger Bands were initially adapted for a financial application. The disclosed system adapts the Bollinger Bands to a health and fitness environment.

A first exemplary weight scaling Bollinger Band chart 500, shown in FIG. 10, presents a trending history of an individual's health index number over a period of time 712, where the chart shows a downward trend. The weight scaling Bollinger Band chart 500 includes a weight axis 510

(located along a vertical axis) and a time axis 512 (located along a horizontal axis. The weight management scale 200 acquires weight measurements 530, 531, 532, 533, 534 (as examples), which are charted in the weight scaling Bollinger Band chart 500. The charted measurements 530, 531, 532, 533, 534 (as examples) indicate a decreasing trend. Bollinger Bands are overlaid onto the weight scaling Bollinger Band chart 500, as illustrated. The Bollinger Bands are aligned with a neutral reference line 520 established at any suitable point, such as an initial weight measurement 530. A first upper band extends between the neutral reference line 520 and a first upper band boundary 522. A second upper band extends between the first upper band boundary 522 and a second upper band boundary 524. Similarly, a first lower band extends between the neutral reference line 520 and a first lower band boundary 523. A second lower band extends between the first lower band boundary 523 and a second lower band boundary 525. When a weight measurement falls within a certain band, the band information is conveyed to the weight management system processing 130. The weight management system processing 130 uses the band information as a component in an analysis to determine if changes in activities, diet, and the like should be suggested to the user.

Additional weight measurements are taken over time, each weight measurement indicated by a like symbol. It is noted that the exemplary weight scaling Bollinger Band chart 500 orients the Bollinger Bands horizontally. The horizontal orientation of the Bollinger Bands indicates that the changes in the user's health are nominal and could be improved.

A second exemplary chart, referred to as a weight scaling Bollinger Band chart 600, shown in FIG. 11, presents a trending history of an individual's health index number over a period of time 612, where the chart shows a downward trend. Elements of the weight scaling Bollinger Band chart 600 are similar to the elements of the weight scaling Bollinger Band chart 500. Like elements of the weight scaling Bollinger Band chart 600 and the weight scaling Bollinger Band chart 500 are numbered the same, except preceded by the numeral '6'. The weight of the user is indicating a downward trend. The Bollinger Bands are oriented having a downward slope over time. The chart presents the upper and lower bounds of the Bollinger Bands are shown adapted to better present the trending improvements of the individual. The downward sloping orientation of the Bollinger Bands indicates that the changes in the user's health are suggesting an improvement.

A third exemplary chart, referred to as a weight scaling Bollinger Band chart 700, shown in FIG. 12, presents a trending history of an individual's health index number over a period of time, where the measurements over time 712 include an outlier period, such as a holiday time band 729. Elements of the weight scaling Bollinger Band chart 700 are similar to the elements of the weight scaling Bollinger Band chart 500. Like elements of the weight scaling Bollinger Band chart 700 and the weight scaling Bollinger Band chart 500 are numbered the same, except preceded by the numeral '7'. The exception is the introduction of the holiday time band 729. During the holiday time band 729, the Bollinger Bands are arched, wherein the arched section accommodates an increase in weight due to extenuating circumstances and accounts for this accordingly. More specifically, the weight management system 100 accommodates extenuating circumstances without impacting or trying to over compensate with changes to the user's weight management system recommended actions 160 (including the user's activities, environment, routines, and the like).

The weight management system 100 can be adapted to return the health index number to a baseline number when the weight management system 100 determines that the respective user fails to submit any predetermined data within a pre-establish period of time. For example, the weight management system 100 can be adapted to return the health index number to the baseline number if the user fails to submit a weight measurement 112 within the pre-establish period of time, such as 7 days.

Although the present disclosure is adapted towards a weight measurement, it is understood that the health index number and other features can be adapted to other health metrics, such as blood pressure, heart rate, fat content, cholesterol, blood sugar level, and the like.

Figure 18:
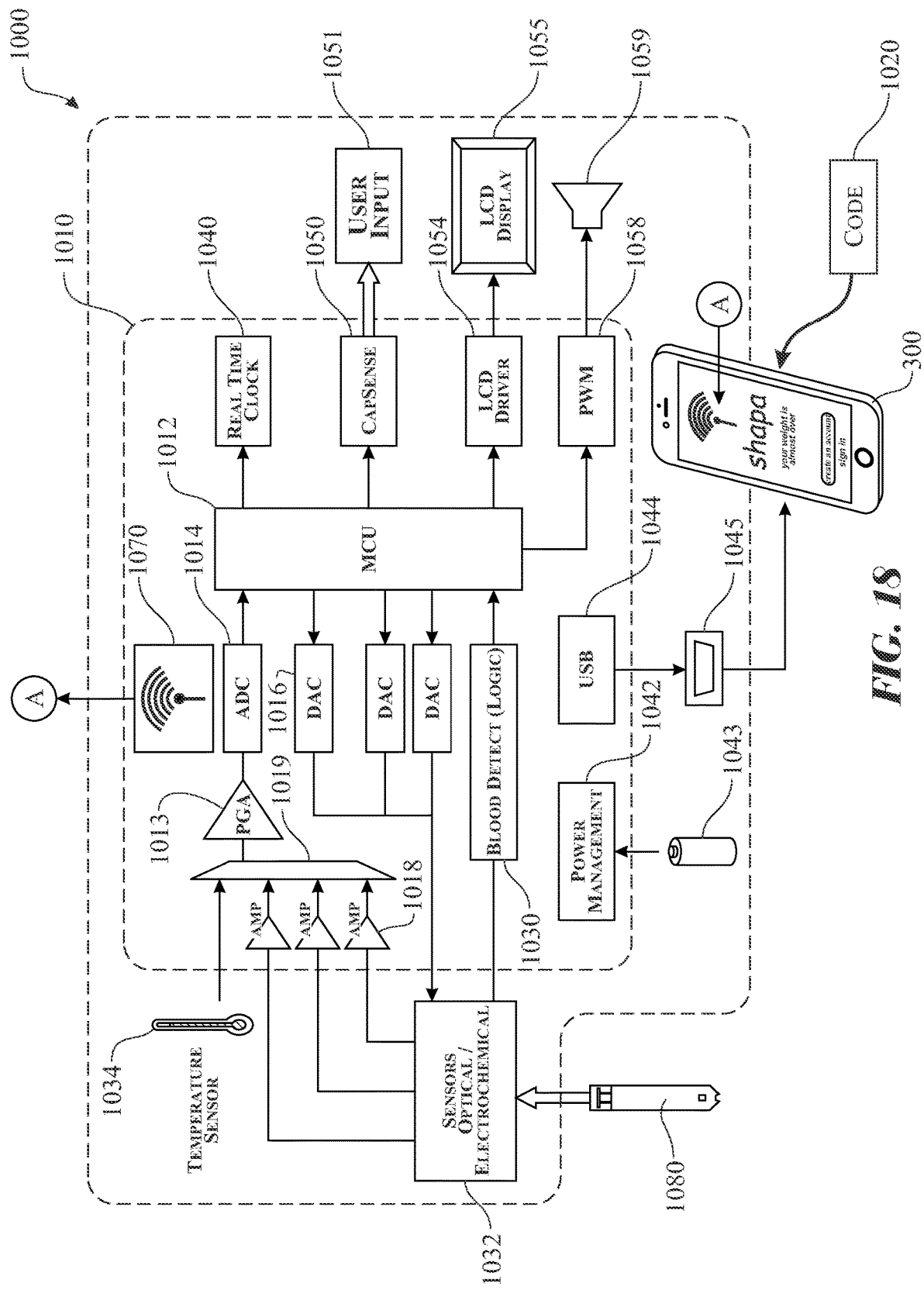
FIG. 18 presents an exemplary schematic diagram introducing a series of exemplary components of a blood glucose level monitoring system employed by the exemplary health and fitness management system originally introduced in FIG. 1.
Figure 19:
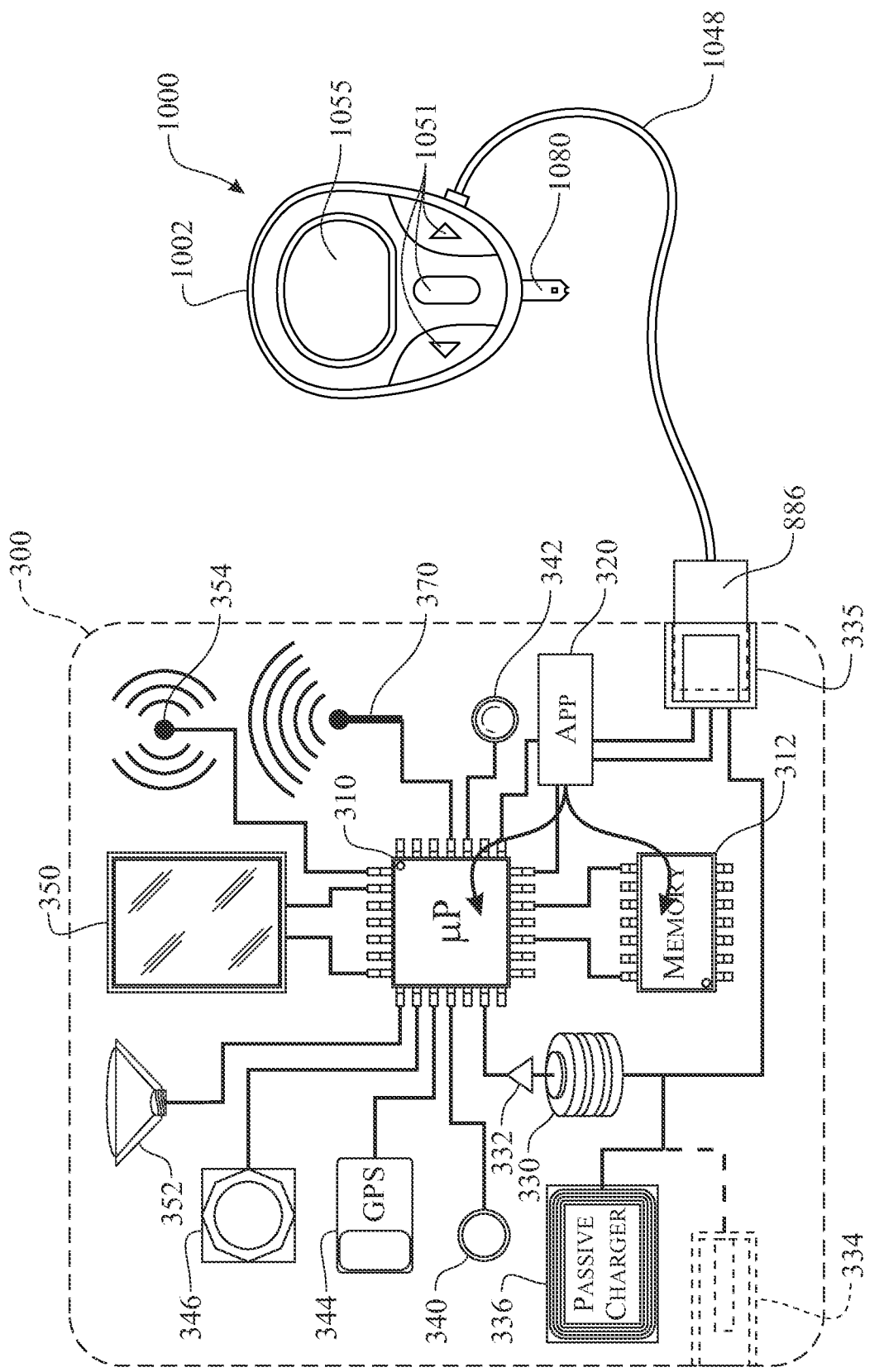
FIG. 19 presents an exemplary schematic diagram introducing a series of exemplary components of the blood glucose level monitoring system adapted for use with the blood glucose level monitoring system employed by the exemplary health and fitness management system originally introduced in FIG. 1.

The disclosure describes a system that employs a scale for obtaining a weight measurement of an individual and a blood pressure monitor for obtaining a blood pressure of an individual. A glucose monitor 1000 (FIGS. 9, 16, 18, and 19) can be substituted for the blood pressure acquisition system 800 described herein. Similar to the blood pressure acquisition system 800, the glucose monitor 1000 would include a communication interface (such as a 1045 for use with a universal serial bus (USB) circuitry 1044 or a wireless communication circuit 1070) for providing acquired information to the portable computing device 300. The glucose monitor 1000 can be manufactured utilizing components replicating functions of any commercially available glucose monitor. Typically, the glucose monitor 1000 includes three separate components or functional elements. First is the meter itself, glucose monitoring system 1000. Usually smaller than a cell phone, it is the brains of the system. Components of an exemplary glucose monitoring system 1000 are presented in FIG. 18. The exemplary glucose monitoring system 1000 includes a glucose monitoring system programmable system on a chip 1010 (such as the blood glucose meter programmable system on a chip provided by Cypress Semiconductor), which significantly simplifies the manufacturing or assembly of the glucose monitoring system 1000. The glucose monitoring system programmable system on a chip 1010 is integrated into a system contained within a glucose monitoring system housing 1002. A portable power supply (for example a battery) 1043 provides power to the glucose monitoring system 1000. The power is managed by a power management circuitry 1042. Blood glucose information is obtained via a sensor bank (optical/electrochemical) 1032. The sensor bank (optical/electrochemical) 1032 receives information from a blood glucose test strip 1080. The information is passed through a series of amplifiers 1018. The output from each of the series of amplifiers 1018 passes through an amplifier 1019 and forwarded through a programmable-gain amplifier (PGA) 1013. The amplified signal is then processed by an analog-to-digital converter (ADC) 1014, which forwards the signal to a microcontroller unit (MCU) 1012. Logic, more specifically, a blood detect logic 1030 analyzes the sample of blood 899 provided on the blood glucose test strip 1080 via the sensor bank (optical/electrochemical) 1032 at the microcontroller unit (MCU) 1012 to determine the blood levels. Commonly, output from the microcontroller unit (MCU) 1012 can be provided to the user in a variety of ways. In one option, the information can be provided via a liquid crystal display (LCD) 1055, which is operated by a liquid crystal display (LCD) driver 1054. In a second option, the information can be provided via an audible output device (speaker) 1059, which is operated by a pulse width modulation (PWM) 1058. In the subject application, the measurement of the blood glucose level would be provided to the portable computing device 300 via a universal serial bus (USB) cable 1048 connected to a universal serial bus (USB) connector 1045 of the glucose monitoring system 1000. Data would be communicated through the universal serial bus (USB) connector 1045 using a universal serial bus (USB) circuitry 1044. Alternatively, data can be provided wirelessly, such as by a wireless communication circuit 1070, which would communication to a like transceiver circuit of the portable computing device 300, as shown by connection "A". In the present application, it is preferred that the value of the blood glucose level is not displayed to the user. Signals from the microcontroller unit (MCU) 1012 can be communicated to the sensor bank (optical/electrochemical) 1032 via the digital-to-analog converter (DAC) 1016. Operation of the glucose monitoring system 1000 can be provided by user inputs. User inputs are provided via a user input device 1051, which can be provided directly to the microcontroller unit (MCU) 1012 or through a capacitive touch sensing technology (capsense) 1050. Time can be provided by a real time clock 1040. The real time clock 1040 provides real time information to the microcontroller unit (MCU) 1012. An optional temperature sensor 1034 can be integrated into the glucose monitoring system programmable system on a chip 1010 to provide temperature data to the glucose monitoring system programmable system on a chip 1010. The elements of the glucose monitoring system 1000 would be contained within a glucose monitoring system housing 1002.

The next component of the system is the blood glucose test strip 1080. The blood glucose test strips 1080 are thin flexible plastic matchsticks between half an inch and an inch long; usually an eighth inch or so wide. The blood glucose test strips 1080 are actually quite a bit more complex than they appear; sandwiched between a top foil 1081 and a bottom foil 1082 is quite a bit of science. The blood glucose test strips 1080 are designed to wick in a small blood sample 899 for analysis by the meter 1000. The blood glucose test strips 1080 are disposable one-shot wonders. A plurality of electrodes is applied to the bottom foil 1082. The electrodes include a fill-trigger electrode 1084, a working electrode 1086, and a reference electrode 1088. An enzyme layer 1089 is commonly included with the working electrode 1086. The top foil 1081 is secured atop of the plurality of electrodes using any bonding material, such as a double sided adhesive 1083, as shown in the exemplary illustration.

Figure 16:
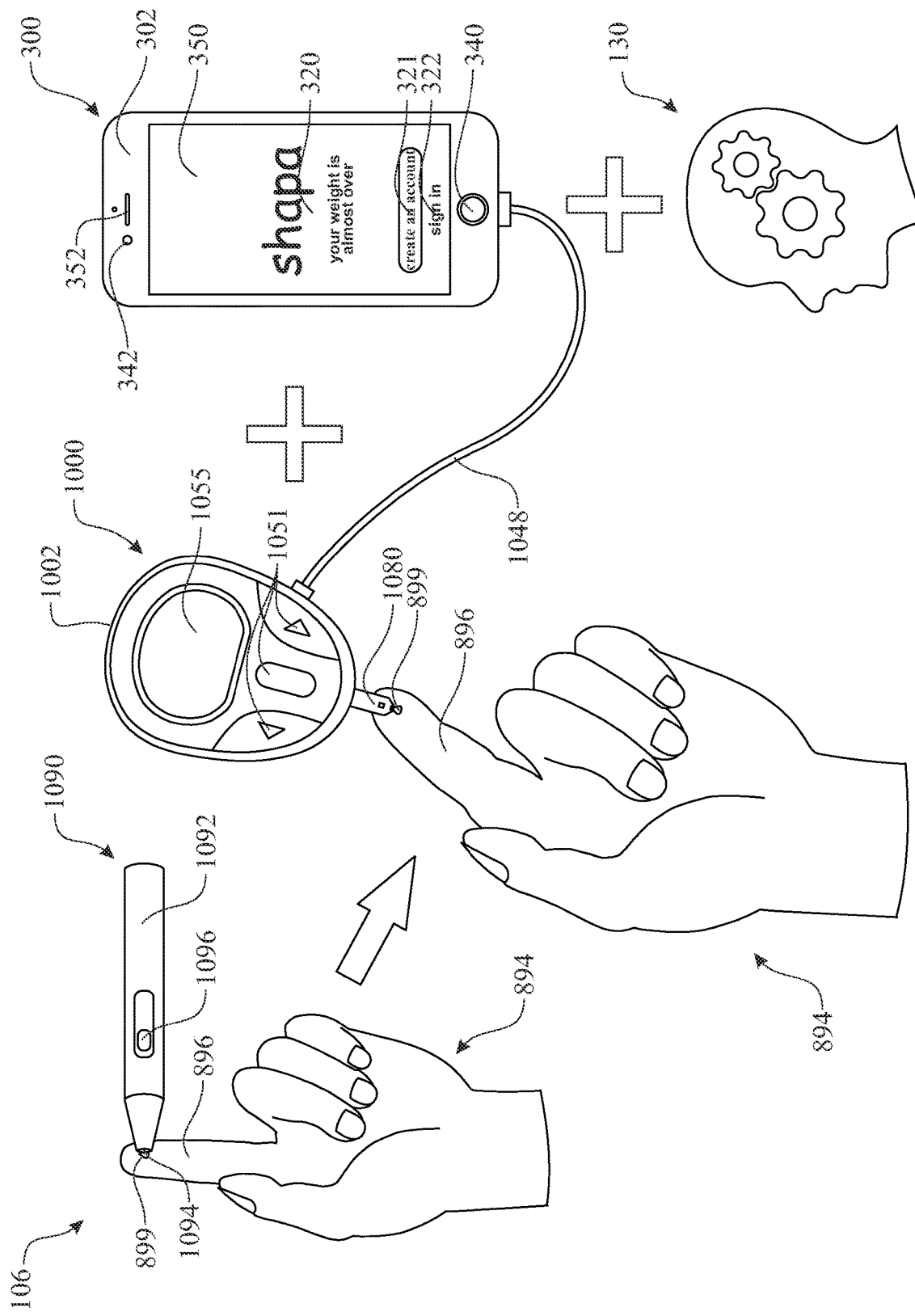
FIG. 16 presents a schematic diagram of third exemplary series of components employed by the exemplary health and fitness management system associated with the operational process flow introduced in FIG. 1.
Figure 17:
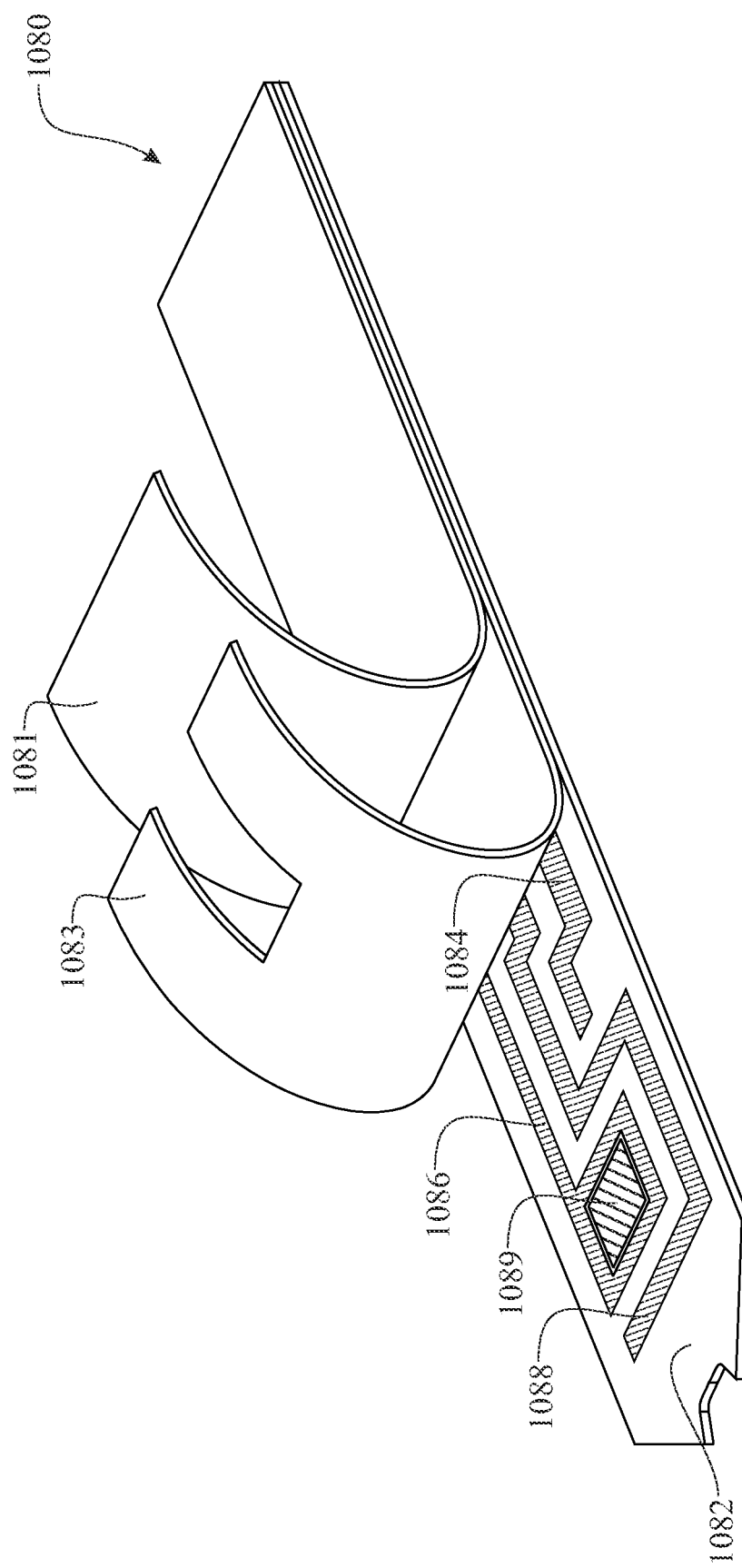
FIG. 17 presents an isometric partial assembly view of a blood glucose test strip identifying the components thereof.

The third part of the glucose monitor 1000 trilogy is the lancing device 1090, which is introduced in FIG. 16. Often vaguely pen-shaped, this is a spring-loaded plastic mechanism whose job it is to poke a small hole in the skin of the patient with minimum pain. The glucose lansing device 1090 includes a glucose lansing device body 1092 (which is often vaguely pen-shaped), a lancet 1094 located at an operational end of the glucose lansing device body 1092 and a lansing trigger 1096. The lansing trigger 1096 operates the spring-loaded plastic mechanism.

The glucose monitor 1000 would be exclusive of any function that would display or otherwise communicate a measured glucose level of an individual. The system can be adapted for use with any biometric data acquisition device.

The process of determining a blood glucose level is illustrated in FIG. 16. In use, the user would employ the glucose lansing device 1090 to draw a user's blood drop specimen 899 from a user's glucose test finger 896 of a user's hand 894. This can be accomplished by inserting a lancet 1094 into the glucose lansing device body 1092. The user would then place the lancet 1094 against skin of the user's glucose test finger 896 and actuate the lansing trigger 1096, causing the lancet 1094 to pierce the skin of the user's glucose test finger 896, thus drawing the user's blood drop specimen 899. An end of the blood glucose test strip 1080 is placed adjacent to the user's blood drop specimen 899, drawing blood from the user's blood drop specimen 899. The glucose monitoring system 1000 processes the sample of provided blood to determine the blood glucose level. The determined blood glucose level is conveyed to the portable computing device 300 via any suitable communication link, such as an exemplary universal serial bus (USB) cable 1048 shown in the illustration. Upon receipt of the blood glucose level, the portable computing device 300 utilizes a glucose level acquisition operating instruction set 1020 in a manner similar to the blood pressure acquisition operating instruction set 820 as described above.

The portable computing device having a color index display 300a can be adapted for use with any biometric data acquisition device, including the weight management scale 200 (as illustrated in FIG. 13), the blood pressure acquisition system 800, the glucose monitoring system 1000, and the like. Similarly, the function provided by the examples presented in FIG. 14 can be adapted for use with any biometric data acquisition device, including the weight management scale 200 (as illustrated in FIG. 13), the blood pressure acquisition system 800, the glucose monitoring system 1000, and the like. The blood pressure output display 900 can be adapted for historical presentation of blood sugar levels when using the glucose monitoring system 1000. This can include blood sugar levels (mg/dl), time of measurement, date of measurement, and the like.

The same metrics system can be adapted to other facets of an individual's lifestyle.

For example, the individual can enter financial information into the system. The system can then utilize the financial information to provide the individual with guidance on their financial habits. This would be accomplished in a manner similar to the use of the individual's weight, where the financial information would be utilized in an algorithm to determine an index number. The index number would then be used by an Application or other computing system operating in accordance with a set of instructions similar to those described above to provide suggestions to the individual to manage their financial condition.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

Element Descriptions

Ref. No. Description 100 weight management system 102 health management system 104 health management system 110 weight management system baseline data 112 wireless scale information 113 blood pressure and/or heart rate information 114 activity tracker 116 Global Position System (GPS) location 118 ancillary information 120 baseline data collection and pattern recognition step 130 weight management system processing 132 weight management system processing steps 140 feedback loop 150 curated content 160 weight management system recommended actions 162 health advice 164 social challenges 166 commercial offers 170 wireless communication link 200 weight management scale 202 weight management scale housing 210 weight management scale microprocessor 212 weight management scale non-volatile digital memory 220 weight management scale operating instruction set 230 weight management scale portable power supply 232 weight management scale power regulator 234 weight management scale line power input 236 weight management scale wireless power charging circuit 240 weight acquisition element 250 weight management scale display 270 weight management scale wireless communication circuit 300 portable computing device 300a portable computing device having a color index display 300b portable computing device having a second exemplary color state display 300c portable computing device having a third exemplary color state display 300d portable computing device having a fourth exemplary color state display 302 portable computing device housing 310 portable computing device microprocessor 312 portable computing device non-volatile digital memory 318 health index number 320 weight management application 320a exemplary first color display 320b exemplary second color display 320c exemplary third color display 320d exemplary fourth color display 320e exemplary fifth color display 321 user account creation icon 322 user account log in icon 323 weight management application Graphical User Interface (GUI) 324 weight management application scheduler 325 weight management application measurements 326 weight management application notifications 327 weight management application questions 330 portable computing device portable power supply 332 portable computing device power regulator 334 portable computing device line power input 335 Universal Serial Bus (USB) port 336 portable computing device wireless power charging circuit 340 portable computing device mechanical user input device 342 portable computing device camera 344 portable computing device Global Position System (GPS) receiver 346 portable computing device accelerometer 350 portable computing device display 352 portable computing device speaker 354 portable computing device haptic feedback generator 370 portable computing device wireless communication circuit 400 weight management system network 410 weight management system network non-volatile remote services 420 web-based application 421 user profile 422 user scheduler 423 weight management system rules 425 weight management questions bank 426 weight management decision engine 429 weight management third-party content 430 weight management third-party application 500 weight scaling Bollinger Band chart 510 weight axis 512 time axis 520 neutral reference line 522 first upper band boundary 523 first lower band boundary 524 second upper band boundary 525 second lower band boundary 530 first exemplary weight measurement 531 second exemplary weight measurement 532 third exemplary weight measurement 533 fourth exemplary weight measurement 534 fifth exemplary weight measurement 535 sixth exemplary weight measurement 600 weight scaling Bollinger Band chart 610 weight axis 612 time axis 620 neutral reference line 621 initial weight reference line 622 first upper band boundary 623 first lower band boundary 624 second upper band boundary 625 second lower band boundary 630 first exemplary weight measurement 631 second exemplary weight measurement 632 third exemplary weight measurement 633 fourth exemplary weight measurement 634 fifth exemplary weight measurement 700 weight scaling Bollinger Band chart 710 weight axis 712 time axis 720 neutral reference line 722 first upper band boundary 723 first lower band boundary 724 second upper band boundary 725 second lower band boundary 729 holiday time band 730 first exemplary weight measurement 731 second exemplary weight measurement 732 third exemplary weight measurement 733 fourth exemplary weight measurement 734 fifth exemplary weight measurement 800 blood pressure acquisition system 802 blood pressure acquisition system electronics assembly housing 810 blood pressure acquisition system microprocessor 814 pressure sensor 820 blood pressure acquisition operating instruction set 835 blood pressure acquisition system connector 840 blood pressure acquisition element (pressure cuff) 842 pressure generator 844 pressure relief control 846 pressure control transfer tube 848 pressure output transfer tube 870 blood pressure acquisition wireless communication circuit 880 communication cable assembly 882 communication cable 884 communication cable first end connector 886 communication cable second end connector 890 user 892 user's upper arm 894 user's hand 896 user's glucose test finger 899 user's blood drop specimen 900 blood pressure output display 910 daily view selection 912 weekly view selection 914 monthly view selection 916 date display 918 date incrementing scroll icon 920 systolic (sys) pressure 922 diastolic (dia) pressure 924 heart beat rate 930 reference chart 932 systolic (sys) pressure column 934 diastolic (dia) pressure column 940 normal blood pressure level reference 942 elevated blood pressure level reference 944 high blood pressure level (stage) reference 946 high blood pressure level (stage) reference 1000 glucose monitoring system 1002 glucose monitoring system housing 1010 glucose monitoring system programmable system on a chip 1012 microcontroller unit (MCU) 1013 programmable-gain amplifier (pga) 1014 analog-to-digital converter (ADC) 1016 digital-to-analog converter (DAC) 1018 amplifier 1019 capacitive touch sensing technology (capsense) 1020 glucose level acquisition operating instruction set 1030 blood detect logic 1032 sensor bank (optical / electrochemical) 1034 temperature sensor 1040 real time clock 1042 power management circuitry 1043 portable power supply (battery) 1044 universal serial bus (USB) circuitry 1045 universal serial bus (USB) connector 1048 universal serial bus (USB) cable 1050 capacitive touch sensing technology (capsense) 1051 user input device 1054 liquid crystal display (LCD) driver 1055 liquid crystal display (LCD) 1058 pulse width modulation (PWM) 1059 audible output device (speaker) 1070 wireless communication circuit 1080 blood glucose test strip 1081 top foil 1082 bottom foil 1083 double sided adhesive 1084 fill-trigger electrode 1086 working electrode 1088 reference electrode 1089 enzyme layer 1090 glucose lansing device 1092 glucose lansing device body 1094 lancet 1096 lansing trigger Exemplary Questionnaire
General Overview:
Ask questions
Wait two weeks
Start producing recommendations daily
Ideally, people are able to (via text?) say that they completed the recommendation at the end of the day
ONLINE QUESTIONNAIRE
Demographics
1. How do you identify?
Female
Male
Other
2. What is your age?
_____
3. What is your height?
_____feet_____inches
4. What is your relationship status?
single
in a relationship
married
divorced 5. How many children do you have?
   0
   1
   2
   3
   4
   5+
   Home
6. Where do you live?
   Urban
   rural
   suburban
7. With whom do you live?
   Alone
   With roommates
   With your significant other or spouse
   With your family members
8. Which of the following do you have within 15 min of your house? Please check all that apply
   Park or green space
   Walking or hiking trails
   Beach
9. How long does it take you to get to the nearest grocery store?
   Under 10 min
   10-20 min
   20-30 min
   30+
10. Do you have a close friend or family member who lives within walking distance from your house?
    yes (how many) _____
    no
    Eating & cooking habits
11. How many times a month does your household go grocery shopping? Use the total number of all members of your household.
    _____
12. Of those times, how many times did you specifically go grocery shopping in the last month?
    _____
13. What do you currently have at home? Check all that apply
    Fresh fruit
    Fresh vegetables
    Frozen fruit
    Frozen vegetables
    Ice cream
    Cake or pastry
    Frozen dinners or frozen pizza
    Fish or seafood
    Chicken
    Turkey
    Red meat such as beef or pork
    Cereal
    Chips
    Candy
    Nuts
    Beans
    Bread
    Soda
    Beer
    Wine
    Hard alcohol
14. In the last week, how many times did you
    Cook, prepare, or pack lunch for yourself? _____
    Cook, prepare, or pack lunch for others? _____
    Cook dinner? _____
15. How many times in the last week did you eat home-cooked meals?
    Breakfast _____
    Lunch _____
    Dinner _____
16. How many times in the last week did you eat out?
    Breakfast
    Lunch
    Dinner
    [Skip if 0] 17. Of these, how many were at a fast food restaurant?
    Breakfast
    Lunch
    Dinner
18. How many times a day on average do you snack? Reflect on the last week to figure this out. A snack=anything eaten in between meals.
    [Skip if 0] 19. In the last week, which snacks did you eat? Please check all that apply
    Candy
    Chips
    Nuts
    Chocolate
    String cheese
    Crackers
    Fruit
    Vegetables
    Ice cream
    Left overs
20. How many times in the last week did you have a dessert after lunch?
    _____
21. How many times in the last week did you have a dessert after dinner?
    _____
    [Skip if 0 for 20 and 21] 22. In the last week, which desserts did you eat? Please check all that apply
    Cake or pie
    Pastry
    Candy
    Chocolate
    Fruit
    Ice cream
    Frozen yogurt
23. What time did you have breakfast yesterday?
    7am
    8am
    9am
    10am
    I did not have breakfast
    [Skip if "I did not have breakfast"] 24. What did beverage did you have with breakfast yesterday? (check all that apply):
    water
    coffee
    tea
    juice
    none of the above
25. What time did you have lunch yesterday?
    11am
    12pm
    1pm
    2pm
    I did not have lunch
26. What time did you have dinner yesterday?
    5pm
    6pm 7pm
8pm
9pm
10pm
I did not have dinner
[Skip if "I did not have dinner"] 27. With whom did you have dinner yesterday?
　Alone
　With a friend(s)
　With my spouse or family
[Skip if "I did not have dinner"] 28. When you had dinner yesterday, what was the setting? check all that apply
　I sat at the dinner table
　The TV was on
　I was in front of my computer / tablet
[Skip if "I did not have dinner"] 29. When you had dinner yesterday, how long did dinner take?
　_____minutes
30. Do you have a dining room or kitchen table with a table and chairs at home?
　Yes
　No
31. In the last month where did you most often eat dinner?
　In the kitchen
　In the dining room
　In the living room
　In my bedroom
Work 32. Where do you usually work?
　I go to work_____days a week
　I work from home_____days a week
　[Skip if "I work from home=0"] 33. How do you usually get to work?
　　walk
　　bike
　　use public transportation
　　drive/carpool
　[Skip if "I work from home>1"] 34. At work, check all that apply:
　　There is a cafeteria that serves food
　　There is a lunch room where you can eat food if you bring it from home
　　There is a refrigerator to store food
　　There is a microwave to heat up food
　　There are at least 3 healthy restaurants nearby
　[Skip if "I work from home"] 35. Are there vending machines at work?
　　Yes
　　No
　[Skip if "No" or "I work from home>1"] 36. Last week, how many times did you get a snack or soda out of the vending machine at work?
　　_____
37. Over the last month, on average, how many hours a day did you work?
　0
　1-6
　6-8
　8-10
　10-12
　Over 12
38. How much physical activity does your work involve?
　Very little - I'm mostly sitting or standing
　Light physical activity such as walking (under half of the time)
　Moderate physical activity such as walking or jogging (over half of the time)
　Heavy physical activity such as lifting 39. Last week, how many times did you eat lunch with another person?
　_____
40. Last week, how many times did you eat lunch:
　At home?_____
　Out?_____
　At my desk at work?_____
　At the cafeteria or lunch room?_____
Free Time
41. Do you have a membership to a gym or exercise facilities?
　Yes
　No
　[Skip if no] 42. Where is the gym or exercise facility? Please check all that apply
　　At home
　　At work
　　Within 15 min drive from home
43. What do you do with free time in the evening? Please check all that apply
　Watch television or play video games
　Socialize with friends
　Read
　Exercise alone
　Exercise with a friend or family member
　Go shopping
　Play with or care for my children
　Attend a cultural event or talk
　Engage in a creative or activity such as painting or playing an instrument
　Engage in an outdoor activity
　Go to a party
　Go to a bar
　Go dancing
　Walk my dog
44. What do you do with free time on the weekend? Please check all that apply
　Watch television or play video games
　Socialize with friends
　Read
　Exercise alone
　Exercise with a friend or family member
　Go shopping
　Play with or care for my children
　Attend a cultural event or talk
　Engage in a creative or activity such as painting or playing an instrument
　Engage in an outdoor activity
　Go to a party
　Go to a bar
　Go dancing
　Walk my dog
45. Which of the following is most accurate about you?
　I love cooking
　Cooking is ok; I wouldn't mind trying to do more of it
　I'm not a big fan of cooking
　I hate cooking
46. Think about the times you felt stressed over the last month. How much stress did each of these cause? [show 5 point scale of none to very much]
　Work
　Finances
　Conflict with a family member, friend, or significant other
　Worrying about my child/children
　Other 47. Please rank the moments when you felt the most stress with 1=the most stress and 6=the least stress
    When I first woke up
    During my commute to work
    While at work
    On my commute home from work
    After arriving home
    When trying to fall asleep
48. Which of the following did you do when you were stressed? [show 5 point scale of never too often]
    Reached out to a friend or family member
    Went for a walk
    Ate comfort food or junk food
    Listened to music
    Exercised
    Drank alcohol
    Went shopping
    Meditated
    Smoked a cigarette
    Used a recreational drug
    Other_____
49. How often do you travel in a typical month?
    almost never
    1-3 days/month
    4-7 days/month
    7-14 days/month
    14+days/month
50. New ideas and projects sometimes distract me from previous ones
    Very much like me
    Mostly like me
    Somewhat like me
    Not much like me
    Not like me at all
51. Setbacks don't discourage me
    Very much like me
    Mostly like me
    Somewhat like me
    Not much like me
    Not like me at all
52. I have been obsessed with a certain idea or project for a short time but later lost interest.
    Very much like me
    Mostly like me
    Somewhat like me
    Not much like me
    Not like me at all
53. I am a hard worker
    Very much like me
    Mostly like me
    Somewhat like me
    Not much like me
    Not like me at all
54. I often set a goal but later pursue a different one
    Very much like me
    Mostly like me
    Somewhat like me
    Not much like me
    Not like me at all
55. I have difficulty maintaining my focus on projects that take more than a few months to complete.
    Very much like me
    Mostly like me
    Somewhat like me
    Not much like me
    Not like me at all
56. I finish whatever I begin.
    Very much like me
    Mostly like me
    Somewhat like me
    Not much like me
    Not like me at all
57. I am diligent.
    Very much like me
    Mostly like me
    Somewhat like me
    Not much like me
    Not like me at all IN-APP QUESTIONS Questions used as "incentive" for daily weigh-in during first two weeks 58. I have a hard time breaking bad habits
    Not at all to very much (5 point scale)
59. I am lazy
    Not at all to very much (5 point scale)
60. I say inappropriate things
    Not at all to very much (5 point scale)
61. I do certain things that are bad for me, if they are fun
    Not at all to very much (5 point scale)
62. I refuse things that are bad for me
    Not at all to very much (5 point scale)
63. I'm good at resisting temptation.
    Not at all to very much (5 point scale)
64. I wish I had more self-discipline
    Not at all to very much (5 point scale)
65. People would say that I have iron self-discipline
    Not at all to very much (5 point scale)
66. Pleasure and fun sometimes keep me from getting work done
    Not at all to very much (5 point scale)
67. I have trouble concentrating
    Not at all to very much (5 point scale)
68. I am able to work effectively toward long-term goals
    Not at all to very much (5 point scale)
69. Sometimes I can't stop myself from doing something, even if I know it is wrong.
    Not at all to very much (5 point scale)
70. I often act without thinking through all the alternatives.
    Not at all to very much (5 point scale Suggested Examples of Feedback Key:
1=Display only once
G=Display with long gaps in between/infrequently
Suggestions for everyone:
Eat dinner with no distractions—no TV, cellphone. Eat slowly and enjoy.
Snack proof your home—put all junk food away in an inconvenient location. The more inconvenient, the better: in your laundry room, in a really hard-to-reach drawer, etc. 1
Buy fruit and put it in a bowl in a prominent area of your kitchen. 1
Eat at least one meal today outdoors. If that's not possible, eat as close as you can to the window with lots of natural light.
Clear your kitchen counters of clutter. Put away all food except for fruit. G
Reorganize your fridge. Move unhealthy items to the back and bring healthy items to the front and center. Store healthy items in transparent containers or plastic wrap. G
Take out a piece of paper and write out the following statement, "I value being healthy because. . . " Complete it with your reasons (e.g. I want to live a long life for my kids, to have more energy, etc). Put this on your fridge. 1

Play slow music during dinner tonight.

Download a new podcast episode. Allow yourself to listen to it only when exercising. Don't have a favorite podcast? Here is a recommended podcast: www.samplepodcast.com Use the Half-Plate Rule for your next meal. Serve whatever you'd like (e.g. protein & starch) on one half, as long as vegetables make up the other half.

Eat something green. For example: lettuce, broccoli, green beans, and green pepper.

Go to bed 30 minutes earlier tonight.

Drink a full glass of water before your next meal.

Cut your screen time 1 hour before bed.

Get colorful! Try to add as much color to your next meal. For example, add bright reds (tomatoes), oranges (carrots), yellows (peppers) or greens (green beans).

Write a message to your 85-year old self. Tell yourself why you're happy you stayed healthy and what sorts of things you got to do in your life as a result.

At your next meal, try eating with chopsticks. If you don't have chopsticks, make sure to put your fork down in between bites while you're chewing. G If 7=With your family members AND 8 at least 1 checked Go for a walk with your family If 8>1 checked Get some fresh air. Go for a 30-min walk or bike ride around your neighborhood or at a nearby park.

If 10=yes OR 43=yes OR 44=yes

Call or message a friend to invite them to go for a walk.

Call or message a friend to make plans that include physical activity. For example, invite them to join you jogging, tennis, hiking, etc.

Call or message a friend to make plans that are not centered around eating or drinking. For example: check out a museum, go to a cultural or art event, play Frisbee® or mini-golf.

If 12>2

Write out a shopping list for your next trip to the grocery store. Include 3 fruits (and 3 vegetables and on your list. How about: apples, strawberries, bananas and green beans, carrots, and broccoli?

Try adding a fruit you don't usually eat to your grocery list. How about plums, mango, pomegranate, or kiwi?

Try adding a vegetable you don't usually eat to your grocery list. How about bok-choy, arugula, or cauliflower?

Try adding a vegetable you don't usually eat to your grocery list. How about asparagus, zucchini, or kale?

Look up a new recipe like www.samplewebsite.com to try and buy the ingredients to make it.

If 13 soda checked

Move your soda from the fridge to your cabinet. G

If 14>2

Try making a favorite recipe but substitute in some different ingredients such as vegetables and spices.

Make one healthy substitution on your grocery list. For example: replace of white pasta with whole wheat pasta or white rice with brown rice.

If 15>2

Measure the plates in your home. Ideally they should measure around 9.5 inches. If they are larger than 11 inches, buy new plates. Colored plates are better than white ones. Something like this: www.samplewebsite.com.

If 18>2

Have a snack, but instead of eating it out of the bag, pour it into a small bowl. Pour one serving's worth.

If 30=yes AND 31=in the kitchen or in the living room or in my bedroom

Eat dinner in your dining room.

If 32 I go to work >2

Snack proof your office—clear unhealthy food from the top of your desk. Put it away in your desk drawers.

Take the stairs instead of the elevator today.

Take the stairs instead of the elevator today. Take 2 at a time.

Bring fruit to work as a snack. If you don't have fruit, buy some.

Buy healthy nuts like almonds. Pre-pack them in small snack bags (about 20 almonds) and bring them to work as a snack.

Bring a water bottle to work. As you drink the water, use each time that you run out as an excuse to get up and stretch your legs a bit when you refill it.

If 32=I go to work >5 or more

Set up 5 glasses on your desk and fill them up with water. Drink them throughout the day.

If 33=use public transportation

Get off one stop earlier than you usually would on your commute and walk instead.

If 33=drive/carpool

Park in a spot that's far from your office and enjoy the extra few steps to decompress before jumping into work mode.

If 33=walk

Challenge yourself—wear comfortable shoes and see if you can get to work extra fast today. Time yourself!

If 33=walk or bike

Switch it up: take a different route to or from work.

If 34=There is a refrigerator to store food

Pack a healthy lunch to bring to bring to work. Pack it the night before so you can grab it and go in the morning.

If 34=There are at least 3 healthy restaurants nearby

Go to the nearest healthy restaurant to your work and get a copy of their menu. Circle the healthiest items and keep this at your desk. 1

If 38=Very little - I'm mostly sitting or standing

Set 3 alarms on your phone to go off during the work day. Space them 1-2 hours apart. Each time an alarm goes off, get up, stretch, and walk around.

If 41=Yes

Pick a time that you'll go to the gym this week. Add it to your calendar.

If 41=yes

Look up a gym or fitness class that you'd like to attend and add it to your calendar.

If 45=I love cooking AND 43=Play with or care for my children

Cook with your child/children tonight. Teach them how to make a healthy recipe.

If 46>4

Write down 3 things you are grateful for. G

If 46>4 AND 7=With roommates, With your significant other or spouse or With your family members At dinner tonight, go around the table and have everyone share good thing that happened today, or one thing they are grateful for.

If 46>6

Watch a funny movie or show. G

Download a funny podcast. Not sure which one to pick? Try www.sample website.com. G Take a relaxing bath. G Call a family member to catch up and tell them you miss them. G If 46>4 AND if 32 I go to work >2

Send a brief email to a colleague and tell them they did a good job on a recent project or assignment. G Send a brief email to a mentor or colleague who has helped you and thank them for their role in supporting you. 1

If 46 Finances >3

Set up an automatic transfer in your bank account from checking to savings. We recommend starting with $25/week. 1

If 49=7-14 days/month or 14+days/month

Stock up on some travel-friendly snacks so you'll have them ready for your next trip. We like 100-calorie almond packs, protein bars, or granola bars. Store them in the suitcase you usually travel with. G If 49=14+days/month Put your sneakers in your suitcase you normally travel with and include a piece of paper that says: "Airport challenge: no moving walkways, escalators, or elevators." This will be a reminder for your next trip.

What is claimed is:

1. A method of managing health and fitness of an individual, the method comprising steps of:
   a) acquiring a health indicating measurement of the individual using a health indicating measurement acquisition device, wherein the health indicating measurement acquisition device is configured to not directly or indirectly convey the health indicating measurement to the individual;
   b) providing an output including the health indicating measurement from the health indicating measurement acquisition device to a computer processing device, wherein the computer processing device is remote from the health indicating measurement acquisition device and operates in accordance with an algorithm included within an operating instruction set;
   c) calculating, by the computer processing device, a health index number of the individual as a function of the output including a value of the health indicating measurement and at least one age value associated with the individual, in accordance with the operating instruction set;
   d) utilizing, by the computer processing device, the individual's health index number to determine a trend of the individual's health and fitness at a current time compared to a previous time;
   e) utilizing, by the computer processing device, the trend of the individual's health and fitness to determine and present guidance, by at least one display device coupled to the computer processing device, to the individual, wherein the guidance is configured to improve the management of the individual's health and fitness; and
   f) presenting, by the at least one display device, at least one of the individual's health index number and the trend of the individual's health and fitness to the individual, wherein the health indicating measurement includes at least one vital sign of a user.

* * * * *